United States Patent [19]

Philibert et al.

[11] Patent Number: 4,540,686

[45] Date of Patent: * Sep. 10, 1985

[54] 3-KETO-19-NOR-$\Delta^{4,9}$-STEROIDS

[75] Inventors: Daniel Philibert, La Varenne Saint-Hilaire; Jean G. Teutsch, Pantin; Germain Costerousse, Saint-Maurice; Roger Deraedt, Pavillons-Sous-Bois, all of France

[73] Assignee: Roussel Uclaf, Paris, France

[ * ] Notice: The portion of the term of this patent subsequent to Oct. 16, 2001 has been disclaimed.

[21] Appl. No.: 618,590

[22] Filed: Jun. 8, 1984

Related U.S. Application Data

[63] Continuation of Ser. No. 469,042, Feb. 23, 1983, Pat. No. 4,477,445.

[30]    Foreign Application Priority Data

Mar. 1, 1982 [FR] France ............................. 82 03338

[51] Int. Cl.³ ..................... C07J 17/00; A61K 31/58
[52] U.S. Cl. ................................. 514/179; 260/397.45
[58] Field of Search ................................. 260/397.45

[56]    References Cited

U.S. PATENT DOCUMENTS 4,233,296  11/1980  Teutsch et al. ................. 260/239.5

FOREIGN PATENT DOCUMENTS 2801416  7/1978  Fed. Rep. of Germany ... 260/239.5

Primary Examiner—Elbert L. Roberts
Attorney, Agent, or Firm—Charles A. Muserlian

[57]    ABSTRACT

Novel 3-keto-19-nor-$\Delta^{4,9}$-steroids of the formula

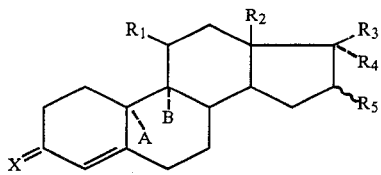

possessing a remarkable antiglucocorticoidal activity.

20 Claims, No Drawings

3-KETO-19-NOR-$\Delta^{4,9}$-STEROIDS

PRIOR APPLICATION

This application is a continuation of U.S. copending patent application Ser. No. 469,042 filed Feb. 23, 1983, now U.S. Pat. No. 4,477,445.

STATE OF THE ART

U.S. Pat. No. 4,233,296 describes steroids being substituted in the 11-position with substituents other than the present formula. U.S. Pat. No. 3,190,796 describes steroids having a hydroxyl in the 11-position. Schonemann et al [European Journal of Medicinal Chemistry, Chimica Therapeutica, Vol. 15, No. 4 (July, August 1980), p. 333–335] describes steroids subtituted in the 11-position with

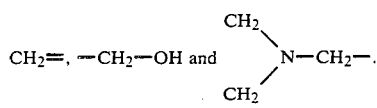

Copending, commonly assigned U.S. patent application Ser. No. 338,077 filed Jan. 8, 1982 now U.S. Pat. No. 4,386,085 and Ser. No. 386,967 filed June 10, 1982 now U.S. Pat. No. 4,447,424 disclose related compounds possessing a different substituent in the 11-position.

OBJECTS OF THE INVENTION

It is an object of the invention to provide the novel steroids of formula I and their non-toxic, pharmaceutically acceptable acid addition salts and a novel process and novel intermediates for their preparation.

It is another object of the invention to provide novel antiglucocorticoid compositions and to a novel method of inducing antiglucocorticoidal activity in warm-blooded animals.

These and other objects and advantages of the invention will become obvious from the following detailed description.

THE INVENTION

The novel steroids of the invention are selected from the group consisting of 3-keto-19-nor-$\Delta^{4,9}$-steroids of the formula

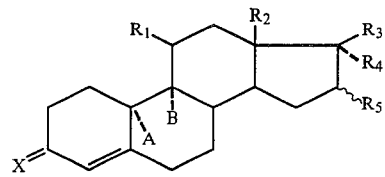

wherein $R_1$ is selected from the group consisting of naphthyl, phenylphenyl, alkyl of 1 to 6 carbon atoms, alkenyl of 2 to 6 carbon atoms optionally containing additional unsaturations, phenoxy, furyl, cycloalkyl of 3 to 6 carbon atoms, thienyl optionally substituted with at least one member of the group consisting of halogen and alkyl and haloalkyl of 1 to 6 carbon atoms and phenyl optionally substituted with at least one member of the group consisting of —OH, halogen, —$CF_3$, alkyl and alkoxy of 1 to 6 carbon atoms, alkenyloxy of 2 to 6 carbon atoms, phenoxy and alkylthio of 1 to 6 carbon atoms optionally oxidized to the sulfoxide or sulfone, $R_2$ is selected from the group consisting of methyl and ethyl, $R_3$ is selected from the group consisting of hydrogen, optionally substituted alkyl of 1 to 6 carbon atoms, optionally substituted alkenyl and alkynyl of 2 to 6 carbon atoms, —OH, acetyl, hydroxyacetyl, carboxyalkoxy of 2 to 4 carbon atoms optionally esterified or salified and hydroxyalkyl of 1 to 6 carbon atoms optionally esterified, $R_4$ is selected from the group consisting of hydrogen, alkylthio and alkoxy of 1 to 12 carbon atoms, trialkylsilyl of 1 to 6 carbon atoms, —CN, —OH and alkyl, alkenyl and alkynyl of up to 12 carbon atoms optionally substituted with at least one member of the group consisting of halogen and alkylamino and dialkylamino of 1 to 6 alkyl carbon atoms, $R_5$ is selected from the group consisting of hydrogen and methyl in the $\alpha$- or $\beta$-position, X is =O or hydroxyimino or alkoxyimino of 1 to 4 carbon atoms in the syn or anti form and A and B are an epoxy or a second bond in the 9(10) position and their non-toxic, pharmaceutically acceptable acid addition salts when $R_4$ is an amino group, with the proviso that A and B are not a second bond in the 9(10)-position when X is =O and $R_5$ is hydrogen and (a) $R_2$ is methyl and ($\alpha$) $R_3$ is —OH and (i) $R_1$ is ethyl or phenyl and $R_4$ is hydrogen or (ii) $R_1$ is ethyl, propyl, isopropyl, vinyl, allyl, isopropenyl, phenyl, 4-fluorophenyl, methoxyphenyl or thienyl and $R_4$ is ethynyl or (iii) $R_1$ is propyl, isopropyl, vinyl, allyl, isopropenyl, 4-methoxyphenyl or thienyl and $R_4$ is methyl and ($\beta$) $R_3$ is acetyl and (i) $R_1$ is ethyl, vinyl or phenyl and $R_4$ is —OH or (ii) $R_1$ is vinyl and $R_4$ is methyl and (b) $R_2$ is ethyl and $R_1$ is vinyl, $R_3$ is —OH and $R_4$ is hydrogen.

When $R_1$ is a substituted thienyl, the substituents may be a halogen such as fluorine, chlorine or bromine, alkyl such as methyl or ethyl and haloalkyl such as trifluoromethyl $R_1$ may be cycloalkyl such as cyclopropyl, cyclobutyl, cyclopentyl or cyclohexyl; phenyl substituted with at least one substituent such as alkyl like methyl, ethyl, propyl, isopropyl, butyl, isobutyl, sec.-butyl, tert.-butyl, pentyl, isopentyl or hexyl; and alkoxy and alkylthio such as methoxy, ethoxy, propoxy, isopropoxy, butoxy, isobutoxy, sec-butoxy, tert-butoxy, pentoxy, hexyloxy, methylthio, ethylthio, propylthio, isopropylthio, butylthio, isobutylthio, sec-butylthio, tert-butylthio, pentylthio, hexylthio; alkenyloxy such as vinyloxy or allyloxy; alkyl such as methyl, ethyl, propyl, isopropyl, butyl, isobutyl, sec.-butyl, tert-butyl, pentyl, isopentyl or hexyl; alkenyl such as vinyl or allyl or propa-1,2-dienyl.

$R_2$ is preferably methyl and $R_3$ is preferably tert.-butoxycarbonylmethoxy or carboxymethoxy optionally salified with an alkali metal, an alkaline earth metal, ammonium or an organic base. Examples of suitable salts are sodium, potassium, lithium, calcium, magnesium, ammonium and salts with an organic base such as methylamine, propylamine, trimethylamine, diethylamine, triethylamine, N,N-dimethyl-ethanolamine, tris(hydroxymethyl)-aminomethane, ethanolamine, pyridine, picoline, dicyclohexylamine, morpholine, benzylamine, procaine, lysine, arginine, histidine and N-methylglucamine. Sodium is the preferred salt. $R_3$ may be substituted with alkylamino or dialkylamino or a halogen, alkylthio, alkoxy or trimethylsilyl.

$R_4$ is preferably methyl, ethyl, ethynyl or prop-1-ynyl or 3-dimethylamino-prop-1-ynyl or 3-amino-prop-1-ynyl. $R_3$ or $R_4$ preferably contain not more than 4 carbon atoms and are especially ethynyl or propynyl.

Among the alkyloximes of X, methoxyimino is preferred.

Examples of suitable acids to form the non-toxic, pharmaceutically acceptable acid addition salts are inorganic acids such as hydrochloric acid, hydrobromic acid, phosphoric acid and sulfuric acid and organic salts such as acetic acid, trifluoroacetic acid, maleic acid, tartaric acid, citric acid, p-toluene sulfonic acid, methanesulfonic acid or benzenesulfonic acid.

Among the preferred compounds of the invention are those wherein $R_1$ is cycloalkyl of 3 to 6 carbon atoms or substituted thienyl, those wherein X is hydroxyimino or alkoxyimino of 1 to 4 carbon atoms in the syn or anti positions, those wherein A and B are an α-epoxy group and those wherein $R_5$ is methyl.

Particularly preferred are those compounds of formula I wherein $R_3$ is —OH, those wherein $R_4$ is propynyl, those wherein $R_2$ is methyl, those wherein $R_5$ is hydrogen, those wherein $R_3$ is acetyl, those wherein $R_4$ is methyl or hydrogen and those wherein $R_1$ is optionally substituted phenyl.

Other preferred compounds of formula I are those wherein $R_1$ is cyclopropyl or phenyl optionally substituted with at least one member of the group consisting of chlorine, fluorine, methylthio, methylsulfonyl, methoxy, hydroxy and allyloxy or chlorothienyl and $R_4$ is propynyl.

Specific preferred compounds of formula I are 11β-(4-chlorophenyl)-17α-(prop-1-ynyl)-Δ$^{4,9}$-estradiene-17β-ol-3-one, 11β-(5-chlorothienyl)-17α-(prop-1-ynyl)-Δ$^{4,9}$-estradiene-17β-ol-3-one, 11β-(3-chlorophenyl)-17α-(prop-1-ynyl)-Δ$^{4,9}$-estradiene-17β-ol-3-one, 11β-(4-methylthio-phenyl)-17α-(prop-1-ynyl)-Δ$^{4,9}$-estradiene-17β-ol-3-one, 11β-(3-fluorophenyl)-17α-(prop-1-ynyl)-Δ$^{4,9}$-estradiene-17β-ol-3-one, 11β-(4-methylthio-phenyl)-17α-methyl-19-nor-Δ$^{4,9}$-pregnadiene-3,20-dione, 11β-(4-methylthiophenyl)-16α-methyl-19-nor-Δ$^{4,9}$-pregnadiene-3,20-dione, 11β-chloropropyl-17α-(propyl-1-ynyl)-Δ$^{4,9}$-estradiene-17β-ol-3-one, 11β-[3-(2-propenyloxy)-phenyl]-17α-(prop-1-ynyl)-Δ$^{4,9}$-estradiene-17β-ol-3-one, 9α,10α-epoxy-11β-(4-methoxy-phenyl)-17α-(prop-1-ynyl)-Δ$^4$-estrene-17β-ol-3-one, 9α,10α-epoxy-11β-(4-methylsulfonylphenyl)-17α-(prop-1-ynyl)-Δ$^4$-estrene-17β-ol-3-one, the anti isomer of 3-hydroxyimino-11β-(3-fluorophenyl)-17α-(prop-1-ynyl)-Δ$^{4,9}$-estradiene-17β-ol, 11β-(4-hydroxyphenyl)-17α-(prop-1-ynyl)-Δ$^{4,9}$-estradiene-17β-ol-3-one and especially 11β-(4-methylthiophenyl)-17α-(prop-1-ynyl)-Δ$^{4,9}$-estradiene-17β-ol-3-one.

The novel process of the invention for the preparation of a compound of formula I comprises reacting a compound of the formula

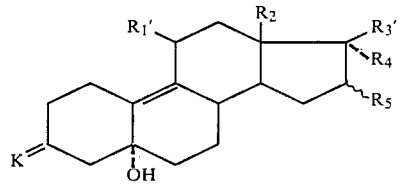

wherein $R_2$, $R_4$ and $R_5$ have the above definitions, K is ketal, thioketal, oxime or methyloxime, $R_3'$ is $R_3$ or a blocked acetyl, $R_1'$ is $R_1$ or phenyl subtituted with a protected —OH with a deshydration agent capable of freeing the protected groups to obtain a compound of the formula

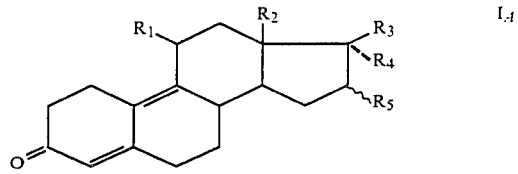

and optionally subjecting the latter to one or more of the following reactions (a) oxidation to obtain a compound of formula I wherein A and B form an epoxy group and when $R_1$ contains a sulfur atom, oxidation to the sulfoxide or sulfonyl form, (b) reaction with hydroxylamine or alkoxyamine to obtain a compound of formula I wherein X is hydroxyimino or alkoxyimino, (c) hydrolyzing and optionally salifying the compound of formula $I_A$ when $R_3$ is esterified carboxyalkoxy, (d) and salification when $R_4$ is alkyl, alkenyl or alkynyl substituted with amino, alkylamino or dialkylamino.

In a preferred mode of the process of the invention, the deshydration agent capable of freeing protected groups which are ketones or hydroxyl is a sulfonic acid resin in its acid form such as a commercial sulfonic acid resin based on polystyrene polymers or a copolymer of styrene and divinylbenzene or a mineral acid such as hydrochloric acid or sulfuric acid in a lower alkanol or perchloric acid in acetic acid or a sulfonic acid such as p-toluenesulfonic acid.

The preferred oxidation agent is a peracid such as m-chloroperbenzoic acid, peracetic acid or perphthalic acid or hydrogen peroxide alone or in the presence of hexachloroacetone or hexafluoroacetone. When there is a number of groups to be oxidized, more than one oxidizing agent may be used. For example, if $R_1$ contains a sulfur atom to be oxidized and a double bond is epoxided, one uses at least three equivalents of oxidizing agent.

The reaction with hydroxylamine or alkoxyamine, especially methoxyamine, is effected preferably in an alkanol such as ethanol and it may be in the form of its acid addition salt, especially its hydrochloride. The optional hydrolysis and salification of the products when $R_3$ is esterified carboxy—is effected under the usual conditions. The hydrolysis may be effected at reflux in an organic solvent such as benzene in the presence of an acid such as p-toluene sulfonic acid or in the presence of a base followed by acidification. The salification may be effected in the presence of sodium hydroxide in ethanol, for example, with a sodium salt such as sodium or potassium carbonate or bicarbonate.

The salification of the amino containing compounds of formula I may be effected by known methods, preferably with hydrogen chloride in an ether solution.

In a preferred mode of the invention, the compounds of formula II are those wherein $R_3'$ is —OH, $R_4$ is propynyl, $R_2$ is methyl and $R_5$ is hydrogen or those wherein $R_3'$ is acetyl, $R_4$ is methyl or hydrogen and $R_1'$ is optionally substituted phenyl or those wherein $R_1'$ is cyclopropyl or chlorothienyl or phenyl optionally substituted with chlorine, florine, methylthio, methylsulfonyl, methoxy, hydroxy or allyloxy and $R_4$ is propynyl.

The novel antiglucocorticoid compositions of the invention are comprised of an antiglucocorticoidally effective amount of at least one compound of formula I or its non-toxic, pharmaceutically acceptable acid addition salts and an inert pharmaceutical carrier. The compositions may be in the form of tablets, dragees, gelules, granules, suppositories, injectable solutions or suspensions, pomades, creams, and gels prepared in the usual manner.

Examples of suitable excipients are talc, gum arabic, lactose, starch, magnesium stearate, cocoa butter, aqueous or non-aqueous vehicles, fatty bodies of animal or vegetable origin, paraffinic derivatives, glycols, diverse wetting agents, dispersants or emulsifiers and preservatives.

The compositions of the invention have remarkable antiglucocorticoid properties as can be seen from the pharmalogical data infra. The study of the products against hormonal receptors shows that the compositions possess progestomimetic activity or anti-progestomimetic, androgenic or antiandrogenic activity.

The compositions are used principally against secondary effects of glucocorticoids and are equally useful against troubles due to a hypersecretion of glucocorticoids and especially against aging in general and are particularly active against hypertension, atherosclerosis, osteoporosis, diabetes, obesity as well as depression of immunity and insomnia. The compositions of the invention also possess antiprogestomimetic activity and are useful for the preparation of original contraceptives and are equally useful against hormonal irregularities and they present an interest in the treatment of hormonodependent cancers.

Some of the compounds of formula I′ and their acid addition salts also possess progestomimetic activity and are useful for the treatment of amenorrhea, dysmenorrhea and luteal insufficiencies.

The compositions of the invention also present antiandrogenic activity making them useful for the treatment of hypertrophia, prostate cancer, hyperandrogenia, anemia, hirsutism and acne.

Among the preferred compositions of the invention are those wherein the active compound is selected from the group consisting of 11β-(4-chlorophenyl)-17α-(prop-1-ynyl)-Δ$^{4,9}$-estradiene-17β-ol-3-one, 11β-(5-chlorothienyl)-17α-(prop-1-ynyl)-Δ$^{4,9}$-estradiene-17β-ol-3-one, 11β-(3-chlorophenyl)-17α-(prop-1-ynyl)-Δ$^{4,9}$-estradiene-17β-ol-3-one, 11β-(4-methylthio-phenyl)-17α-(prop-1-ynyl)-Δ$^{4,9}$-estradiene-17β-ol-3-one, 11β-(3-fluorophenyl)-17α-(prop-1-ynyl)-Δ$^{4,9}$-estradiene-17β-ol-3-one, 11β-(4-methylthiophenyl)-17α-methyl-19-nor-Δ$^{4,9}$-pregnadiene-3,20-dione, 11β-(4-methylthiophenyl)-16α-methyl-19-nor-Δ$^{4,9}$-pregnadiene-3,20-dione, 11β-cyclopropyl-17α-(prop-1-ynyl)-Δ$^{4,9}$-estradiene-17β-ol-3-one, 11β-[3-(2-propenyloxy)-phenyl]-17α-(prop-1-ynyl)-Δ$^{4,9}$-estradiene-17β-ol-3-one, 9α,10α-epoxy-11β-(4-methoxyphenyl)-17α-(prop-1-ynyl)-Δ$^{4}$-estrene-17β-ol-3-one, 9α,10α-epoxy-11β-(4-methylsulfonylphenyl)-17α-(prop-1-ynyl)-Δ$^{4}$-estrene-17β-ol-3-one, the anti isomer of 3-hydroxyimino-11β-(3-fluorophenyl)-17α-(prop-1-ynyl)-Δ$^{4,9}$-estradiene-17β-ol, 11β-(4-hydroxyphenyl)-17α-(prop-1-ynyl)-Δ$^{4,9}$-estradiene-17β-ol-3-one and especially 11β-(4-methylthiophenyl)-17α-(prop-1-ynyl)-Δ$^{4,9}$-estradiene-17β-ol-3-one.

The novel method of the invention of inducing antigluococorticoid activity in warm-blooded animals, including humans, comprises administering to warm-blooded animals an antigluococorticoidally effective amount of at least one compound of formula I and their non-toxic pharmaceutically acceptable acid addition salts. The compounds may be administered orally, rectally, topically or parenterally and the usual daily dose is 0.15 to 15 mg/kg depending on the specific condition being treated and the specific compound being used.

Another facet of the invention are novel intermediates of the formula

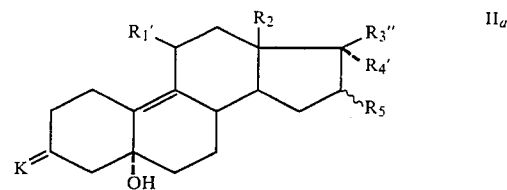

wherein $R_1'$ is selected from the group consisting of optionally substituted thienyl, furyl, cycloalkyl of 3 to 6 carbon atoms, naphthyl, phenylphenyl, alkyl of 1 to 6 carbon atoms, alkenyl of 2 to 6 carbon atoms optionally containing several double bonds and phenyl optionally substituted with at least one member of the group consisting of halogen, —OH, protected hydroxy, —CF$_3$ alkyl and alkoxy of 1 to 6 carbon atoms, alkenyloxy of 2 to 6 carbon atoms, phenoxy and alkylthio of 1 to 6 carbon atoms optionally oxidized to sulfoxide or sulfonyl, $R_2$ is selected from the group consisting of methyl and ethyl, $R_3''$ is selected from the group consisting of hydrogen, alkyl of 1 to 6 carbon atoms, optionally substituted alkenyl and alkynyl of 2 to 6 carbon atoms, —OH, acetyl optionally protected in the form of a ketal, hydroxyacetyl, esterified carboxyalkoxy of 2 to 4 carbon atoms and acyloxyalkyl and $R_4'$ is selected from the group consisting of hydrogen, —OH, alkyl of 1 to 12 carbon atoms and alkenyl and alkynyl of 2 to 12 carbon atoms optionally substituted with a member of the group consisting of alkylamino, dialkylamino, halogen, alkylthio, alkoxy, trialkylsilyl and cyano with the alkyls having 1 to 6 carbon atoms or $R_3''$ is —CN and $R_4'$ is a blocked —OH in the form of an easily cleavable ether, $R_5$ is selected from the group consisting of hydrogen and —CH$_3$ in the α- or β-position, K is blocked ketone in the form of a ketal, thioketal, oxime or methyloxime except the products wherein K is (1,2-ethanediyl) acetal, $R_5$ ia hydrogen and (a) $R_2$ is methyl and (α) $R_3''$ is —CN, $R_4'$ is trimethylsilyloxy and $R_1$ is selected from the group consisting of phenyl, methyl, ethyl, propyl, isopropyl, tert.-butyl, vinyl, allyl, isopropenyl, o- and p-methoxyphenyl, thienyl, methoxyvinyl and p-fluorophenyl or (β) $R_3''$ is —OH, $R_4'$ is ethynyl and $R_1'$ is selected from the group consisting of ethyl, propyl, isopropyl, vinyl, isopropenyl, allyl, thienyl and o- and p-methoxyphenyl or (γ) $R_3''$ is acetyl, (i) $R_4'$ is —OH and $R_1'$ is ethyl, vinyl or phenyl or (ii) $R_4'$ is methyl and $R_1'$ is vinyl and (b) $R_2$ is ethyl, $R_3''$ is —OH, $R_1'$ is vinyl and $R_4'$ is hydrogen.

In these compounds the thienyl group substituents and the cycloalkyls may be as described above and $R_1'$ substitutents are the same as those of $R_1$. The —OH may be protected with a known protective group such as acyls like acetyl, chloroacetyl, trifluoroacetyl and phenoxyacetyl or other groups such as tetrahydropyrannyl, trityl, benzyl, benzhydryl or trimethylsilyl.

The acyloxyalkyl group of $R_3''$ is preferably 1-acetoxyethyl and the easily cleavable ether of $R_4'$ is preferably trimethylsilyl. The ketone blocking group is preferably ethanediyl.

Among the preferred compounds of formula II$_a$ are those wherein R$_3$" is —OH, those wherein R$_4$' is propynyl, those wherein R$_5$ is hydrogen and those wherein R$_2$ is —CH$_3$.

Among the preferred definitions of R$_1$' are cycloalkyl, especially cyclopentyl, phenyl optionally substituted with chlorine, fluorine, methylthio, methylsulfonyl, hydroxymethoxy and/or allyloxy and chlorothienyl.

The compounds of formula II$_a$ may be prepared by reacting a compound of the formula

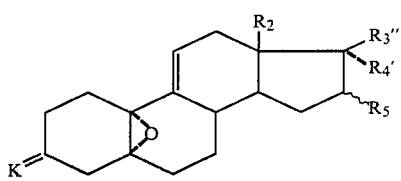   III wherein K, R$_2$, R$_3$", R$_4$' and R$_5$ have the above definitions with a compound of the formulae CuLi(R$_1$')$_2$ or R$_1$'MgHal or R$_1$'Li wherein R$_1$' has the above definition and Hal is a halogen in the presence of a catalytic amount of a cuprous halide to obtain the corresponding compound of formula II$_a$ which, if desired, may be subjected in any order to one or more of the following reactions: (a) reaction with a complex of lithium acetylide and ethylenediamine with a compound of formula II$_a$ wherein R$_3$" is —CN and R$_4$' is an —OH protected by an easily cleavable ether to obtain a compound of formula II$_a$ wherein R$_3$" is —OH and R$_4$' is ethynyl, (b) or reacting with a methyl magnesium halide the compound IIa wherein R$_3$" is —CN and R$_4$' is —OH in the form of an easily cleavable ether to obtain a compound of formula II$_a$ wherein R$_3$" is acetyl and R$_4$' is —OH and (c) removal of the —OH or acetyl protecting groups.

When the reactant (R$_1$')$_2$CuLi is used, the reaction temperature is preferably −100° C. to 0° C. and when the reactants R$_1$'Li or R$_1$'MgHal are used, Hal is preferably bromine or chlorine and the reaction is effected at −40° C. to 0° C. in the presence of a catalytic amount of cuprous bromide or chloride. The cuprous halide may optionally be present in the form of a complex with dialkylsulfide.

When it is desired to use an organic solvent or mixtures thereof, the solvent may be ether, isopropyl ether or tetrahydrofuran. In a preferred mode of the process when R$_1$' is other than allyl, it is preferred to introduce the 11β-substituent using R$_1$'MgBr in the presence of a catalytic amount of cuprous chloride at −40° to −20° C. in ether and/or tetrahydrofuran. When R$_1$' is allyl, it is preferred to introduce the 11β-substituent by reaction with (R$_1$')$_2$CuLi at −90° to −10° C.

The compounds of formula II$_a$ wherein R$_3$" is —OH and R$_4$' is alkyl, alkenyl or alkynyl of up to 12 carbon atoms may also be prepared by reacting a compound of the formula

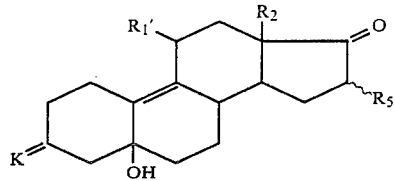   IV wherein K, R$_1$', R$_2$ and R$_5$ have the above definitions with an alkyl, alkenyl or alkynyl magnesium halide.

The compounds of formula IV may be prepared by reacting a compound of the formula

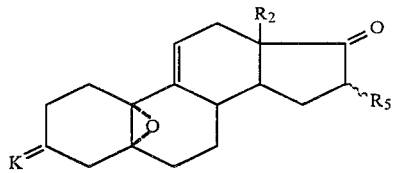   V wherein R$_2$, R$_5$ and K have the above definitions with a compound of the formula (R$_1$')$_2$CuLi or R$_1$'MgHal or R$_1$'Li as described above.

The compounds of formulae III and V are known and can be easily prepared by known processes. They can generally be prepared by oxidizing a compound of the formula

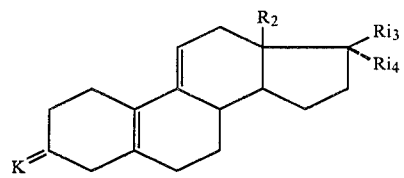

wherein K has the above definition and Ri$_3$ and Ri$_4$ have the same values as R$_3$" and R$_4$', respectively or taken together are =O with hydrogen peroxide in the presence of a catalyst or with an organic per acid.

The following compounds are examples of compounds falling within the scope of formula I:

| R$_1$ | R$_2$ | R$_3$ | R$_4$ |
|---|---|---|---|
| HO—⟨⟩— | CH$_3$ | OH | —C≡C—H |
| " | " | " | —C≡C—Cl |
| " | " | " | —CH$_2$—C≡C—H |
| " | " | " | —CH$_2$—CH$_3$ |
| " | " | " | —C≡C—S—CH$_3$ |
| " | " | " | —C≡C—CH$_2$—CH$_3$ |
| " | " | —C≡C—H | —OH |
| OH—⟨⟩— | " | " | —OH |

-continued

[Structure: steroid skeleton with R1, R2 on one ring carbon, R3, R4 on another, with ketone (O=) on left ring]

| R₁ | R₂ | R₃ | R₄ |
|---|---|---|---|
| " | " | −C(=O)−CH₂OH | H |
| " | " | OH | −C≡C−H |
| " | " | " | −C≡C−CH₃ |
| " | " | " | −C≡C−Cl |
| " | " | " | −CH₂−C≡C−H |
| " | " | " | −CH₂−CH₃ |
| CH₃S−C₆H₄− | " | " | −CH₂−CH₃ |
| " | " | " | −C≡C−H |
| " | " | " | −C≡C−Cl |
| " | " | " | −C≡C−CH₂−CH₃ |
| " | " | " | −CH₂−C≡C−H |
| " | " | " | −CH₂−CH=CH₂ |
| " | −C≡C−H | −OH | |
| " | −C(=O)−CH₂OH | −H | |
| (CH₃)₂CH−C₆H₄− | " | " | H |
| " | " | −OH | −C≡C−H |
| " | " | " | −CH₂−C≡C−H |
| " | " | " | −CH₂−CH=CH₂ |
| " | " | " | −CH₂CH₃ |
| " | " | " | −CH₂CN |
| " | " | " | −CH₃ |
| " | " | " | −C(=O)−C(CH₃)₃ (geminal dimethyl C=O) |
| CH₃O−C₆H₄− | " | " | −CH₃ |
| " | " | OH | −CH₂−C≡C−H |
| " | " | " | −CH₂−CH=CH₂ |
| " | " | " | −CH₂CH₃ |
| " | " | " | −CH₂CN |
| C₆H₅−C₆H₄− | " | " | −CH₂−CH=CH₂ |
| " | " | " | −CH₂−C≡C−H |
| " | " | " | −CH₂−CH₃ |
| " | " | " | −CH₂CN |
| " | " | " | −CH₃ |
| " | " | " | −C(=O)−C(CH₃)₃ |

In the following examples there are described several preferred embodiments to illustrate the invention. However, it should be understood that the invention is not intended to be limited to the specific embodiments. The starting materials for Examples 1 to 58 are prepared in Prepations 1 to 57.

PREPARATION 1

3,3-ethylenebisoxy-11β-(2'-thienyl)-17α-(prop-1-ynyl)-Δ⁹-estrene-5α,17β-diol

STEP A:

3,3-bismethoxy-17α-(prop-1-ynyl)-Δ⁵⁽¹⁰⁾,⁹⁽¹¹⁾-estradiene-17β-ol

Propyne was bubbled for 2 hours under nitrogen in to 350 ml of a solution of 1.1M of ethyl magnesium bromide per liter of tetrahydrofuran cooled to 0° C. while in an ice bath to keep the temperature at 10° C. and the temperature was allowed to rise to 20° C. while continuing to bubble propyne to obtain a solution of propyne magnesium bromide. A solution of 50 g of 3,3-bismethoxy-Δ⁵⁽¹⁰⁾,⁹⁽¹¹⁾-estradiene-17-one in 240 ml of tetrahydrofuran and 2 drops of triethylamine was added at 20° C. to the solution and the mixture was stirred for 75 minutes and was poured in aqueous iced ammonium chloride solution. The mixture was stirred for 15 minutes and was extracted with ether. The organic phase was washed with aqueous saturated sodium bicarbonate solution containing 2 drops of pyridine, was dried and evaporated to dryness under reduced pressure to obtain 62.4 g of residue. 974 mg of residue were chromatographed over silica gel and eluted with a 3-1 ether-petroleum ether (b.p.=60° to 80° C.) mixture to obtain 744 mg of product which was crystallized from a hot mixture of 5.5 ml of isopropyl ether, 0.4 ml of methylene chloride and traces of pyridine. The mixture was filtered and concentrated and crystallization was induced. The mixture was vacuum filtered and the product was rinsed with isopropyl ether and dried to obtain 444 mg of 3,3-bismethoxy-17α-(prop-1-ynyl)-Δ⁵⁽¹⁰⁾,⁹⁽¹¹⁾-estradiene-17β-ol melting at 138° C.

STEP B:

3,3-ethylenebisoxy-17α-(prop-1-ynyl)-Δ⁵⁽¹⁰⁾,⁹⁽¹¹⁾-estradiene-17β-ol

A mixture of 88.5 g of the product of Step A in 442.5 ml of glycol was heated under nitrogen to 60° C. with stirring and 4.425 g of pyridine hydrochloride were added thereto. The mixture was stirred at 60° C. for 15 minutes and was then cooled to 20° C. During the cooling at 40° C., 17.7 ml of triethylamine were added and the suspension at 20° C. was poured into 3 liters of iced water. The mixture was held at 0° C. for one hour and was vacuum filtered. The product was rinsed with water and dried to obtain 75.4 g of 3,3-ethylenebisoxy-17α-(prop-1-ynyl)-Δ⁵⁽¹⁰⁾,⁹⁽¹¹⁾-estradiene-17β-ol melting at 135°–140° C.

STEP C:

3,3-ethylenebisoxy-5α,10α-epoxy-17α-(prop-1-ynyl)-Δ⁹⁽¹¹⁾-estrene-17β-ol 1.8 ml of hexafluoroacetone sesquihydrate were added at 0° C. to a mixture of 30 g of the product of Step B in 150 ml of methylene chloride and 2 drops of pyridine and then 4.35 ml of 85% oxygenated water were added to the mixture dropwise. The mixture was stirred at 0° C. for 72 hours and was then poured with stirring into a mixture of 250 g of ice and 500 ml of 0.2N sodium thiosulfonate solution. The mixture was extracted with methylene chloride and the organic phase was washed with water, dried and evaporated to dryness under reduced pressure to obtain 31.6 g of 3,3-ethylenebisoxy-5α10α-epoxy-17α-(prop-1-ynyl)-Δ$^{9(11)}$-estrene-17β-ol.

STEP D:
3,3-ethylenebisoxy-17α-(prop-1-ynyl)-11β-(2'-thienyl)-Δ$^9$-estrene-5α,17β-diol 0.82 g of cupric chloride were added under nitrogen at −25° C. to 162 ml of a solution of 1.05M of thienyl magnesium bromide per liter of tetrahydrofuran and the mixture was stirred for 15 minutes. A solution of 15 g of the product of Step C in 80 ml of tetrahydrofuran was added dropwise to the mixture while keeping the temperature below −20° C. and the mixture was stirred under nitrogen at −25° C. for 17 hours and at 0° C. for 2 hours and was then poured with stirring into an aqueous iced ammonium chloride solution. The mixture was extracted with ether and the organic phase was washed with water, dried and evaporated to dryness under reduced pressure. The 18.8 g of residue were chromatographed over silica gel and was eluted with a 9-1 chloroform-ethyl acetate mixture to obtain 9.85 g of 3,3-ethylenebisoxy-17α-(prop-1-ynyl)-11β-(2'-thienyl)-Δ$^9$-estrene-5α,17β-diol melting at 250° C.

PREPARATION 2
3,3-ethylenebisoxy-11β-(p-fluorophenyl)-17α-(prop-1-ynyl)-Δ$^9$-estrene-5α,17β-diol Using the procedure of Step D of Example 1, p-fluorophenyl magnesium bromide and 3,3-ethylenebisoxy-5α,10α-epoxy-17α-(prop-1-ynyl)-Δ$^{9(11)}$-estrene-17β-ol were reacted in the presence of cupric chloride in tetrahydrofuran to obtain after chromatography 3,3-ethylenebisoxy-11β-(p-fluorophenyl)-17α-(prop-1-ynyl)-Δ$^9$-estrene-5α,17β-diol with a specific rotation of $[α]_D^{20} = −57.5° ± 1.5°$ (c=1% in chloroform).

PREPARATION 3
3,3-ethylenebisoxy-11β-(p-trifluoromethylphenyl)-17α-(prop-1-ynyl)-Δ$^9$-estrene-5α,17β-diol Using the procedure of Step D of Example 1, p-trifluoromethylphenyl magnesium bromide and 3,3-ethylenebisoxy-5α,10α-epoxy-17α-(prop-1-ynyl)-Δ$^{9(11)}$-estrene-17β-ol were reacted to obtain 3,3-ethylenebisoxy-11β-(p-trifluoromethylphenyl)-17α-(prop-1-ynyl)-Δ$^9$-estrene-5α,17β-diol with a specific rotation of $[α]_D^{20} = −56° = ±2.5°$ (c=0.4% in chloroform).

PREPARATION 4
3,3-bismethoxy-11β-methyl-17α-(prop-1-ynyl)-Δ$^9$-estrene-5α,17β-diol

STEP A:
3,3-bismethoxy-5α,10α-epoxy-17α-(prop-1-ynyl)-Δ$^{9(11)}$-estrene-17β-ol 8.5 ml of hexafluoroacetone sesquihydrate were added all at once with stirring under nitrogen to a mixture of 62.4 g of 3,3-bismethoxy-17α-(prop-1-ynyl)-Δ$^{5(10),9(11)}$-estradiene-17β-ol prepared as in preparation 1 in 280 ml of methylene chloride at 0° C. and 10.1 ml of 85% oxygenated water were added thereto dropwise. The mixture was stirred at 0° C. for 41 hours and was poured into a mixture of 1.4 liters of 0.5M/l of sodium bisulfite solution, 200 g of ice and 5 drops of pyridine. The mixture was stirred for 15 minutes and was extracted with methylene chloride containing 2 drops of pyridine. The organic phase was washed with water containing 2 drops of pyridine. The organic phase was washed with water containing traces of pyridine, dried and evaporated to dryness under reduced pressure to obtain 63.8 g of 3,3-bismethoxy-5α,10α-epoxy-17α-(prop-1-ynyl)-Δ$^{9(11)}$-estrene-17β-ol.

STEP B:
3,3-bismethoxy-11β-methyl-17α-(prop-1-ynyl)-Δ$^9$-estrene-5α,17β-diol 60 ml of 1.74M of methyl lithium in ether were added over 30 minutes to a mixture of 11.4 g of cuprous iodide and 120 ml of ether under nitrogen at 0° C. and the mixture was stirred at 0° C. for 30 minutes after which a solution of 5.5 g of the product of Step A in 50 ml of tetrahydrofuran was added thereto dropwise over 30 minutes. The mixture was stirred at 0° C. for 2 hours and was poured into iced aqueous ammonium chloride solution. The mixture was stirred at room temperature for one hour and was extracted with ether. The organic phase was washed with water, dried and evaporated to dryness under reduced pressure to obtain 5.7 g of residue. 6.8 g of residue were chromatographed over silica gel and eluted with a 9-1 methylene chloride-acetone mixture containing 0.1% of triethylamine to obtain 4.05 g of 3,3-bismethoxy-11β-methyl-17α-(prop-1-ynyl)-Δ$^9$-estrene-5α,17β-diol melting at 155° C. and having a specific rotation of $[α]_D^{20} = 80° ± 2°$ (c=1% in chloroform).

PREPARATION 5
3,3-bismethoxy-11β-(propa-1,2-dienyl)-17α-(prop-1-ynyl)-Δ$^9$-estrene-5α,17β-diol Gaseous allene was bubbled through 300 ml of dry tetrahydrofuran at 0° C. until about 18 to 20 g were dissolved and the mixture was cooled to −70° C. after which 180 ml of a solution of 1.35N n-butyllithium in n-hexane was added thereto dropwise over 30 minutes. The mixture was stirred at −70° C. for 30 minutes to obtain a suspension of allenyllithium to which 24.66 g of a complex of dimethylsulfide and cupric bromide were added in small fractions over 15 minutes. The mixture was stirred at −70° C. for 90 minutes and a solution of 11 g of 3,3-bismethoxy-5α,10α-epoxy-17α-(prop-1-ynyl)-Δ$^{9(11)}$-estrene-17β-ol in 60 ml of anhydrous tetrahydrofuran was added thereto dropwise at −70° C. over 10 minutes. The temperature was allowed to slowly rise to −20° C. (±5° C.) and the mixture was stirred at that temperature under nitrogen for 18 hours and was poured with stirring into iced aqueous ammonium chloride solution. The mixture was stirred at room temperature for one hour and was extracted with ether. The organic phase was washed with water, dried and evaporated to dryness under reduced pressure. The 11.2 g of residue were chromatographed over silica gel and eluted with a 9-1 methylene chloride-acetone mixture containing 0.1% of triethylamine to obtain 6.6 g of 3,3-bismethoxy-11β-(propa-1,2-dienyl)-17α-(prop-1-ynyl)-Δ$^9$-estrene-5α,17β-diol with a specific rotation of $[α]_D^{20} = −25° ± 1°$ (c=1% in chloroform).

PREPARATION 6
3,3-bismethoxy-11β-tert.-butyl-17α-(prop-1-ynyl)-Δ$^9$-estrene-5α,17β-diol Using the procedure of preparation 1, 13.8 ml of a solution of 0.65M of tert.-butyl magnesium chloride in tetrahydrofuran and 1.1 g of 3,3-bisomethoxy-5α,10α- epoxy-17α-(prop-1-ynyl)-Δ⁹⁽¹¹⁾-estrene-17β-ol were reacted and the mixture was stirred at −20° C. for 3 hours to obtain 3,3-bismethoxy-11β-tert.-butyl-17α-(prop-1-ynyl)-Δ⁹-estrene-5α,17β-diol melting at 148°–150° C.

PREPARATION 7

3,3-bismethoxy-11β-(2-furyl)-17α-(prop-1-ynyl)-Δ⁹-estrene-5α,17β-diol

Using the procedure of preparation 5, 3,3-bismethoxy-5α,10α-epoxy-17α-(prop-1-ynyl)-Δ⁹⁽¹¹⁾-estrene-17β-ol and difuryl cupolithium were condensed to obtain 3,3-bismethoxy-11β-(2-furyl)-17α-(prop-1-ynyl)-Δ⁹-estrene-5α,17β-diol with a specific rotation of $[\alpha]_D^{20} = -62 \pm 1.5°$ (c=1% in chloroform).

PREPARATIONS 8 TO 28

Using the procedure of preparation 1, the starting products listed in the following Table were reacted to obtain the compounds of the Table.

| | STARTING MATERIALS | FINAL PRODUCTS | CONDITIONS |
|---|---|---|---|
| Preparation 8: magnesium bromide | 3,3-ethylene-bis-oxy-5α,10α-epoxy-17α-(prop-1-ynyl)-Δ⁹⁽¹¹⁾-estrene-17β-ol | 3,3-ethylenebisoxy-11β-(4-methyl-phenyl)-17α-(prop-1-ynyl)-Δ⁹-estrene-5α,17β-diol m.p. = 172° C. $[\alpha]_D^{20} = -70° \pm 1.5°$ (c = 0.9% CHCl₃) | 2 hours at −20° C. |
| Preparation 9: 3-methyl-phenyl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β-(3-methyl-phenyl)-17α-(prop-1-ynyl)-Δ⁹-estrene-5α,17β-diol m.p. 206° C. $[\alpha]_D^{20} = -72.5° \pm 1.5°$ (c = 1% CHCl₃) | 90 minutes at −20° C. |
| Preparation 10: 4-chloro-phenyl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β-(4-chloro-phenyl)-17α-(prop-1-ynyl)-Δ⁹-estrene-5α,17β-diol m.p. 180° C. $[\alpha]_D^{20} = -62° \pm 2°$ (c = 1% CHCl₃) | 1 hour at −10° C. |
| Preparation 11: 2-chloro-thien-5-yl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β-(5-chloro-thienyl)-17α-(pro-1-ynyl)-Δ⁹-estrene-5α,17β-diol m.p. = 204° C. $[\alpha]_D^{20} = -23° \pm 1°$ (c = 1% CHCl₃) | 18 hours at −10° C. |
| Preparation 12: 3-chloro-phenyl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β-(3-chloro-phenyl)-17α-(prop-1-ynyl)-Δ⁹-estrene-5α,17β-diol m.p. 191° C. $[\alpha]_D^{20} = -67.5° \pm 2.5°$ (c = 1% CHCl₃) | 1 hour at −20° C. |
| Preparation 13: 3-methoxy-phenyl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β-(3-methoxy-phenyl)-17α-(prop-1-ynyl)-Δ⁹-estrene-5α,17β-diol m.p. 228° C. $[\alpha]_D^{20} = -74° \pm 2°$ (c = 0.5% CHCl₃) | 1 hour at −20° C. |
| Preparation 14: 4-methoxy-phenyl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β-(4-methoxy-phenyl)-17α-(prop-1-ynyl)-Δ⁹-estrene-5α,17β-diol m.p. 226° C. $[\alpha]_D^{20} = -68° \pm 2.5$ (c = 1% CHCl₃) | 2 hours at −20° C. |
| Preparation 15: 3,4-bismethoxy-phenyl magnesium bromide | 3,3-ethylenebisoxy-5α,10α-epoxy-17α-(prop-1-ynyl)-17α-(prop-1-ynyl)-Δ⁹estrene estrene-17β-ol | 3,3-ethylenebisoxy-11β-(3,4-bismethoxy-5α,17β-diol m.p. = 230° C. $[\alpha]_D^{20} = -67° \pm 2°$ (c = 0.85% CHCl₃) | 2 hours at −15° C. |
| Preparation 16: 3-trifluoromethyl-phenyl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β-(3-trifluoromethyl-phenyl)-17α-(prop-1-ynyl)-Δ⁹-estrene-5α,17β-diol m.p. = 179° C. $[\alpha]_D^{20} = -58° \pm 2°$ (c = 0.8% CHCl₃) | 30 minutes at −20° C. |
| Preparation 17: 3-trifluoromethyl-4-chloropyenyl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β(3-trifluoromethyl-4-chloro.phenyl17α-(prop-1-ynyl)-Δ⁹-estrene-5α,17β-diol $[\alpha]_D^{20} = -47.5° \pm 1.5°$ (c = 0.9% CHCl₃) | 30 minutes at −10° C. |
| Preparation 18: 2-naphthyl magnesium bromide | 3,3-ethylenebisoxy-5α,10β-epocy-17α-(prop-1-ynyl)-Δ⁹⁽¹¹⁾-estrene-17β-ol | 3,3-ethylenebisoxy-11β-(2-naphthyl)-17α-(prop-1-yny)-α⁹-estrene-5α,17β-diol m.p. 276.5° C. $[\alpha]_D^{20} = -14° \pm 2°$ (c = 0.5% CHCl₃) | 30 minutes at −15° C. |
| Preparation 19: 4-phenoxy-phenyl magesium bromide | 3,3-ethylenebisoxy-5α,10β-epoxy-17α-(prop-1-ynyl)-Δ⁹⁽¹¹⁾-estrene-17β-ol | 3,3-ethylenebisoxy-11β-(4-phenoxy-phenyl)-17α-(prop-1-ynyl)-Δ⁹-estrene 5α,17β-diol m.p. = 163° C. $[\alpha]_D^{20} = -68° \pm 1.5°$ (c = 1% CHCl₃) | 45 minutes at −10° C. |
| Preparation 20: phenyl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β-phenyl-17α-(prop-1-ynyl)-Δ⁹-estrene-5α,17β-diol m.p. = 234° C. $[\alpha]_D^{20} = -74° \pm 2.5°$ (c = 0.5% CHCl₃) | 3 hours 15 min. at −25° C. + 16 hours at 0 C. |
| Preparation 21: | | | |

-continued

| STARTING MATERIALS | FINAL PRODUCTS | CONDITIONS |
|---|---|---|
| 3-bromo phenyl magnesium bromide | 3,3-ethylenebisoxy-5α,10α-epoxy-17α-(prop-1-ynyl)-Δ$^{9(11)}$-estrene-17β-ol | 3,3-ethylenebisoxy-11β-(3-bromo-phenyl)-17α-(prop-1-ynyl)-Δ$^9$-estrene-5α,17β-diol<br>$[\alpha]_D^{20} = -61° \pm 1.5°$ (c = 1% CHCl$_3$) | 1 night at −20 C. |
| Preparation 22:<br>4-bromo phenyl magnesium bromide | 3,3-ethylenebisoxy-5α,10α-epoxy-17α-(prop-1-ynyl)-Δ$^{9(11)}$-estrene-17β-ol | 3,3-ethylenebisoxy-11β-(4-bromo-phenyl)-17α-(prop-1-ynyl)-Δ$^9$-estrene-5α,17β-diol<br>$[\alpha\pi_D^{20} = -55° \pm 2°$ (c = 0.8% CHCl$_3$) | 30 minutes at −15° C. |
| Preparation 23:<br>4-methyl-thiophenyl magnesium bromide | 3,3-ethylenebisoxy-5α,10α-epoxy-17α-(prop-1-ynyl)-Δ$^{9(11)}$-estrene-17β-ol | 3,3-ethylenebisoxy-11β-(4-methylthio phenyl)-17α-(prop-1-ynyl)-Δ$^9$-estrene-5α,17β-diol m.p. = 190 ° C. then 214° C.<br>$[\alpha]_D^{20} = -57° \pm 1.5°$ (c = 1% CHCl$_3$) | 2 hours at −20° C. |
| Preparation 24:<br>3-thienyl magnesium bromide | 3,3ethylenebisoxy-5α,10α-epoxy-17α-(prop-1-ynyl)-Δ$^{9(11)}$-estrene-17β-ol | 3,3-ethylenebisoxy-11β-(3-thienyl)-17 α-(prop-1-ynyl)-Δ$^9$-estrene-5α,17β diol m.p. = 240° C.<br>$[\alpha]_D^{20} = -38° \pm 2.5°$ (c = 1% CHCl$_3$) | 1 hour at −20 ° C. |
| Preparation 25:<br>propyl magnesium bromide | 3,3-ethylenebisoxy-5α,10α-epoxy-17α-(prop-1-ynyl)-Δ$^{9(11)}$-estrene-17β-ol | 3,3-ethylenebisoxy-11β-propyl-17α-(prop-1-ynyl)-Δ$^9$-estrene-5α,17βdiol m.p. = 192° C.<br>$[\alpha]_D^{20} = -108.5° \pm 3°$ (c = 1% CHCl$_3$) | 1 hour at −20 ° C. |
| Preparation 26:<br>3-fluoro-phenyl magnesium bromide | 3,3-ethylenebisoxy-5α,10α-epoxy-17α-(prop-1-ynyl)-Δ$^{9(11)}$-estrene-17β-ol | 3,3-ehtylenebisoxy-11β-(3-fluoro-phenyl)-17α-(prop-1-ynyl)-Δ$^9$-estrene-5α,17β-diol F = 228° C.<br>$[\alpha]_D^{20} = -58.5° \pm 2.5°$ (c = 1% CHCl$_3$) | 1 hour at −15° C. |
| Preparation 27:<br>3-phenyloxy-phenyl magnesium bromide | 3,3-ethylenebisoxy-5α,10α-epoxy-17α(prop-1-ynyl)-Δ$^{9(11)}$-estrene-17β-ol | 3,3-ethylene-bis-oxy-11β-(3-phenyloxy-phenyl)-17α-(prop-1-ynyl)-Δ$^9$-estrene-5α,17β-diol m.p. = 190° C.<br>$[\alpha]_D^{20} = -59.5° \pm 1.5°$ (c = 1% CHCl$_3$) | 45 minutes at −20 ° C. |
| Preparation 28:<br>4-phenyl-phenyl magnesium bromide | 3,3-ethylenebisoxy-5α,10α-epoxy-17α-(prop-1-ynyl)-Δ$^{9(11)}$-estrene-17β-ol | 3,3-ethylenebisoxy-11β-(4-phenyl-phenyl)-17α-(prop-1-ynyl)-Δ$^9$-estrene-5α,17β-diol m.p. = 165° C.<br>$[\alpha]_D^{20} = -52° \pm 2°$ (c = 1% CHCl$_3$) | 1 hour at −20 ° C. |

PREPARATION 29

3,3-ethylenebisoxy-11β-(2'-methylprop-1'-enyl)-17α-trimethylsilyloxy-Δ$^9$-estrene-5α-ol-17β-carbonitrile 32 ml of a solution of 0.95M of 2-methylprop-1-enyllithium in ether were added dropwise at −40° C. to a suspension of 3.1 g of a complex of dimethylsulfide-cupric bromide in 30 ml of tetrahydrofuran and then 4.16 g of the 3-(1,2-ethanediyl)-acetal of 5α,10α-epoxy-17α-trimethylsilyloxy-17β-cyano-Δ$^{9(11)}$-estrene-3-one were added thereto. The mixture stood at −30° C. for 30 minutes and was then poured into aqueous ammonium chloride solution. The mixture was extracted with ether and the organic phase was dried and evaporated to dryness under reduced pressure. The 5.45 g of residue were chromatographed over silica gel and eluted with an 8-2 benzene-ethyl acetate mixtue to obtain 450 mg of 3,3-ethylenebisoxy-11β-(2'-methylprop-1'-enyl)-17α-trimethylsilyloxy-Δ$^9$-estrene-5α-ol-17β-carbonitrile melting at 154° C.

Analysis: C$_{28}$H$_{42}$O$_4$NSi Calculated: %C 69.38; %H 8.73; %N 2.89; Found: %C 69.4; %H 9.0; %N 2.9.

PREPARATION 29A 3,3-ethylenebisoxy-11β-(2'-methylprop-1'-enyl)-17α-ethynyl-Δ$^9$-estrene-5α,17β-diol A solution of 5.45 g of the product of Preparation 29 in 50 ml of ethylenediamine was stirred under nitrogen at 50° C. while adding 6 g of a complex of acetylidelithium and ethylenediamine in small fractions and the mixture was stirred at 50° C. for 3 hours and was poured into a mixture of ice and water. The mixture was extracted with ether and then with chloroform and the organic phases were dried and evaporated to dryness under reduced pressure. The residue was chromatographed over silica gel and eluted with a 7-3 benzeneethyl acetate mixture containing 0.1% of triethylamine to obtain 2.763 g of product with a Rf=0.3. The latter was crystallized from isopropyl ether to obtain 3,3-ethylenebisoxy-11β-(2'-methylprop-1'-enyl)-17α-ethynyl-Δ$^9$-estrene-5α,17β-diol melting at 208° C. as well as 0.26 g of the corresponding 17-keto compound.

Analysis: C$_{26}$H$_{36}$O$_4$ Calculated: %C 75.69; %H 8.80; Found: %C 75.9; %H 8.8.

PREPARATION 30

3,3-ethylenebisoxy-11β-(3-methoxyphenyl)-17α-trimethylsilyloxy-Δ$^9$-estrene-5α-ol-17β-carbonitrile Using the procedure of Preparation 1, the product of Preparation 29 and 3-methoxyphenyl magnesium bromide were reacted to obtain 9.406 g of 3,3-ethylenebisoxy-11β-(3-methoxyphenyl)-17α-trimethylsilyloxy-Δ$^9$-estrene-5α-ol-17β-carbonitrile melting at 166° C.

Analysis: C$_{31}$H$_{43}$NO$_5$Si Calculated: %C 69.23; %H 8.06; %N 2.60; Found: %C 69.4; %H 8.1; %N 2.6.

PREPARATION 30A 3,3-ethylenebisoxy-11β-(3-methoxyphenyl)-19-nor-Δ⁹-pregnene-5α,17α-diol-20-one 20 ml of a solution of 1.3M of methyl magnesium bromide in tetrahydrofuran was concentrated to obtain a 2M solution by evaporation of 7 ml of tetrahydrofuran and then 2.9 g of the product of Preparation 30 were added thereto. The mixture was refluxed overnight and 10 ml of a solution of 1.3M of methyl magnesium bromide were added thereto. 5 ml of tetrahydrofuran were distilled and the mixture was heated at 100° C. for 7 hours and was then poured into iced aqueous ammonium chloride solution. The mixture was extracted with ether and the organic phase was dried and evaporated to dryness under reduced pressure. The residue was chromatographed over silica gel and eluted with a 6-4 benzene-ethyl acetate mixture containing 0.1% of triethylamine to obtain 1.722 g of 3,3-ethylenebisoxy-11β-(3-methoxyphenyl)-19-nor-Δ⁹-pregnene-5α,17α-diol-20-one which after crystallization from a mixture of isopropyl ether and methylene chloride melted at 190° C.

Analysis: $C_{29}H_{38}O_6$ Calculated: %C 72.17; %H 7.94; Found: %C 72.5; %H 8.0.

PREPARATION 31

3,20-bisethyleneketal of 11β-propyl-17α-methyl-19-nor-Δ⁹-pregnene-5α-ol-3,20-dione

STEP A: 3,20-bisethyleneketal of 17α-methyl-19-nor-Δ⁵⁽¹⁰⁾,⁹⁽¹¹⁾-pregnadiene-3,20-dione 1.5 g of p-toluenesulfonic acid monohydrate were added to a solution of 21 g of 17α-methyl-19-nor-Δ⁴,⁹-pregnadiene-3,20-dione in a mixture of 200 ml of methylene chloride, 200 ml of ethylene glycol and 100 ml of ethyl orthoformate and the mixture was refluxed for 7 hours. 2 ml of triethylamine were added thereto and a portion of the solvent was distilled. Water was added to the mixture which was filtered and the product was washed with water and dissolved in methylene chloride. The solution was dried and isopropyl ether was added thereto. The mixture was concentrated to obtain 22.65 g of 3,20-bisethyleneketal of 17α-methyl-19-nor-Δ⁵⁽¹⁰⁾,⁹⁽¹¹⁾-pregnadiene-3,20-dione. The analytical sample was obtained by chromatography and crystallization from isopropyl ether to obtain a product melting at 175° C.

Analysis: $C_{25}H_{36}O_4$ Calculated: %C 74.96; %H 9.06; Found: %C 75.0; %H 9.1.

STEP B: 3,20-bisethyleneketal of 5α,10α-epoxy-17α-methyl-19-nor-Δ⁹⁽¹¹⁾-pregnene-3,20-dione 450 mg of sodium bicarbonate were added with stirring at 0° C. to a solution of 100 mg of the product of Step A in 2 ml of methylene chloride and then 0.1 ml of chloral followed by 0.1 ml of oxygenated water (110 volumes) were added thereto. After 4 hours, reaction was complete and the mixture was poured into aqueous sodium thiosulfate solution. The mixture was extracted with methylene chloride and the organic phase was dried and evaporated to dryness under reduced pressure to obtain 98 mg of 3,20-bisethyleneketal of 5α,10α-epoxy-17α-methyl-19-nor-Δ⁹⁽¹¹⁾-pregnene-3,20-dione.

STEP C: 3,20-bisethyleneketal of 11β-propyl-17α-methyl-19-nor-Δ⁹-pregnene-5α-ol-3,20-dione Using the procedure of Preparation 1, the product of Step B and propyl magnesium bromide were reacted at −30° C. for 2 hours to obtain 3,20-bisethyleneketal of 11β-propyl-17α-methyl-19-nor-Δ⁹-pregnene-5α-ol-3,20-dione.

PREPARATION 31A 3,20-bisethyleneketal of 11β-vinyl-17α-methyl-19-nor-Δ⁹-pregnene-5α-ol-3,20-dione Using the procedure of Preparation 1, the product of Preparation 31 and vinyl magnesium bromide were reacted for 2 hours at −30° C. to obtain 3,20-bisethyleneketal of 11β-vinyl-17α-methyl-19-nor-Δ⁹-pregnene-5α-ol-3,20-dione melting at 192° C.

ANALYSIS: $C_{27}H_{40}O_5$ Calculated: %C 72.94; %H 9.07; Found: %C 72.7; %H 9.2.

PREPARATIONS 32 TO 35

Using the procedure of Preparation 1, the reactants listed in the following Table were reacted.

|  | STARTING MATERIALS |  | FINAL PRODUCTS | CONDITIONS |
|---|---|---|---|---|
| Preparation 32: |  |  |  |  |
| 4-methyl-thiophenyl magnesium bromide | 3,20-bisethyleneketal of 17α-methyl-5α,10α-epoxy-19-nor-Δ⁹⁽¹¹⁾-pregnene-3,20-dione (prepared as in preparation 31) |  | 3,3-20,20-bisethylenebisoxy-17α-methyl-11β-(4-methyl-thiophenyl)-19-nor-Δ⁹-pregnene-5α-ol | dropwise addition at −15° C. |
| Preparation 33: |  |  |  |  |
| Dimethyl cuprolithium | 3,20-bisethyleneketal of 16α-methyl-5α,10α-epoxy-19-nor-Δ⁹⁽¹¹⁾-pregnene-3,20-dione described in French patent No. 2,423,486 |  | 3,3-20,20-bisethylenebisoxy-11β-16α-dimethyl-19-nor-Δ⁹-pregnene-5α-ol m.p. = 140° C. | 1 hour at 0° C. |
| Preparation 34: |  |  |  |  |
| 4-methyl-thiophenyl magnesium bromide | 3,3-30-bisethyleneketal of 16α-methyl-5α,10α-epoxy-19-nor-Δ⁹⁽¹¹⁾-pregnene-3,20-dione described in French patent No. 2,423,486 |  | 3,3,20,20-bisethylenebisoxy-16α-methyl-11β-(4-methyl-thiophenyl)-19-nor-Δ⁹-pregnene-5α-ol m.p. = 189° C. | 1 hour at −15° C. |
| Preparation 35: |  |  |  |  |
| Cyclopropyl cuprolithien (J. Org. Chem. 41, p. 3629 1976) | 3,3-ethylenebisoxy-5α,10α-epoxy-17α-(prop-1-ynyl)-Δ⁹⁽¹¹⁾-estrene-17β-ol |  | 11β-cyclopropyl-3,3-ethylenebisoxy-17α-(prop-1-ynyl)-Δ⁹-estrene-5α,17β-diol | 30 minutes at −70° C. and 3 hours at −40° C. |

PREPARATION 36

Tert.-butyl [3,3-ethylenebisoxy-11β-(3-methoxyphenyl)-17α-(prop-1-ynyl)-Δ⁹-17α-estrene-5α-ol-17-yl]-oxyacetate 3.2 ml of a solution of 1.25M of butyllithium per liter of n-hexane were added dropwise at −40° C. to a solution of 960 mg of 3,3-ethylenebisoxy-11β-(3-methoxyphenyl)-17α-(prop-1-ynyl)-Δ⁹-estrene-5α,17β-diol prepared by preparation 13 in 30 ml of tetrahydrofuran and the temperature was allowed to rise to room temperature. Then, 1.3 ml of tert.-butyl bromoacetate were added thereto dropwise and after 90 minutes, the mixture was poured into aqueous ammonium chloride solution. The mixture was extracted with ether and the organic phase was dried and evaporated to dryness to obtain tert.-butyl [3,3-ethylenebisoxy-11β-(3-methoxyphenyl)-17α-(prop-1-ynyl)-Δ⁹-17α-estrene-5α-ol-17-yl]-oxyacetate.

PREPARATIONS 39 TO 41

Using the procedure of Preparation 1, the products in the following Table were prepared.

|  | STARTING MATERIALS | FINAL PRODUCTS | CONDITIONS |
|---|---|---|---|
| Preparation 39: | | | |
| 4-isopropyl-phenyl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β-(4-isopropyl-phenyl)-17α-(prop-1-ynyl)-Δ⁹-estrene-5α,17β-diol m.p. = 194° C. $[\alpha]_D^{20} = -66.5° \pm 2.5°$ (c = 0.5% CHCl₃) | 1 hour at −20° C. then 1 hour at 0° C. |
| Preparation 40: | | | |
| 3-methyl-thio-phenyl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β-(3-methyl-thiophenyl)-17α-(prop-1-ynyl)-Δ⁹-estrene-5α,17β-diol m.p. = 250° C. $[\alpha]_D^{20} = -65.6° \pm 2°$ (c = 0.7% CHCl₃) | 90 minutes at = 15° to −20° C. |
| Preparation 41: | | | |
| 3-(2-propenyloxy)-phenyl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β-[3-(propenyloxy)-phenyl]-17α-(prop-1-ynyl)-Δ⁹-estrene-5α,17β-diol m.p. 165° C. $[\alpha]_D^{20} = -71° \pm 2.5°$ (c = 0.8% CHCl₃) | 16 hours at −20° C. |

PREPARATION 42

3,3-ethylenebisoxy-11β-(thien-2-yl)-17α-methyl-19-nor-Δ⁹-pregnene-5α,21-diol-20-one

STEP A:

3,3-ethylenebisoxy-5α,10α-epoxy-17α-methyl-19-nor-Δ⁹⁽¹¹⁾-pregnene-21-ol-20-one 19.6 ml of a solution of n-butyllithium in n-hexane were added over 12 minutes at −50° C. to a mixture of 120 ml of tetrahydrofuran and 6.6 ml of N-cyclohexyl-isopropylamine and then 8.9 g of 3,3-ethylenebisoxy-17α-methyl-19-nor-Δ⁵⁽¹⁰⁾,⁹⁽¹¹⁾-pregnadiene-20-one were added thereto with stirring. The mixture was stirred at −35° to −40° C. for one hour and then 17.4 g of an oxidation agent of oxodiperoxopyridino-(hexamethyl-phosphoramido)-molybdenum IV [Bull. Soc., (1969), p. 1481] were added thereto. The mixture was stirred at −30° to −35° C. for 90 minutes and was then poured into ice and water. The mixture was extracted with ethyl acetate and the organic phase was washed with water, dried and evaporated to dryness under reduced pressure. The residue was chromatographed over silica gel and eluted with benzene to obtain 4.03 g of 3,3-ethylenedioxy-17α-methyl-19-nor-Δ⁵⁽¹⁰⁾,⁹⁽¹¹⁾-pregnadiene-21-ol-20-one. 7.8 ml of a solution of one mole of hexafluoroacetone hydroperoxide per liter of methylene chloride were added at 0° to 5° C. to a solution of 1.826 g of the above product in 18.3 ml of methylene chloride and the mixture stood at 0° to 5° C. for 175 minutes and was poured into aqueous 0.5M sodium thiosulfate solution. The mixture was extracted with chloroform and the organic phase was washed with water, dried and evaporated to dryness to obtain 3,3-ethylenebisoxy-5α,10α-epoxy-17α-methyl-19-nor-Δ⁹⁽¹¹⁾-pregnene-21-ol-20-one.

STEP B:

3,3-ethylenedioxy-11β-(thien-2-yl)-17α-methyl-19-nor-Δ⁹-pregnene-5α,21-diol-20-one 300 mg of cupric chloride were added to 40 ml of a solution of 0.5M of thienyl magnesium bromide per liter of tetrahydrofuran and the mixture was held at −20° to −25° C. for 30 minutes. A solution of 2.02 g of the product of Step A in 20 ml of anhydrous tetrahydrofuran was added thereto dropwise and the mixture stood at −20° to −25° C. for 2 hours and was then poured into aqueous ammonium chloride solution. The mixture was extracted with ether and the organic phase was dried to obtain 2.218 g of resin. The latter was chromatographed over silica gel and eluted with a 1-1 benzene-ethyl acetate mixture to obtain 701 mg of 3,3-ethylenedioxy-11β-(thien-2-yl)-17α-methyl-19-nor-Δ⁹-pregnene-5α,21-diol-20-one melting at 204° C. and having an Rf=0.29.

PREPARATIONS 43 and 49

|  | STARTING MATERIALS | FINAL PRODUCTS | CONDITIONS |
|---|---|---|---|
| Preparation 43: | | | |
| cyclopentyl magnesium bromide | 3,3-ethylenebisoxy-5α,10α-epoxy-17α-(prop-1-ynyl)-Δ⁹⁽¹¹⁾-estrene-17β-ol | 3,3-ethylenebisoxy-11β-cyclopentyl-17α-(prop-1-ynyl)-Δ⁹-estrene-5α,17β-diol $[\alpha]_D^{20} = -98° \pm 2°$ (c = 1% CHCl₃) | immediate at −30° C. |
| Preparation 49: | | | |
| 4-(3-methyl-butyl thio)-phenyl magnesium | 3,3-ethylenebisoxy-5α,10α-epoxy-17α-(prop-1-ynyl)-Δ⁹⁽¹¹⁾-estrene-17β-ol | 3,3-ethylenebisoxy-11β-[4-(3-methyl-butyl)-thiophenyl]-17α-(prop-1-ynyl)-Δ⁹-estrene-5α,17β-diol | 1 hour at −20° C. |

| STARTING MATERIALS | FINAL PRODUCTS | CONDITIONS |
|---|---|---|
| bromide | $[\alpha]_D^{20} = -52° \pm 1.5°$ (c = 0.5% $CHCl_3$) | |

PREPARATION 48

3,3-ethylenedioxy-11β-(3-methoxyphenyl)-17α-methyl-20R-acetoxy-19-nor-Δ⁹-pregnene-5α-ol

STEP A:
3,3-ethylenedioxy-17α-methyl-20R-acetoxy-19-nor-Δ⁵,⁹-pregnadiene 2.7 g of p-toluene sulfonic acid hydrate and then 40 ml of methylene chloride was added with stirring at 25° C. to a suspension of 45 g of 17α-methyl-20R-acetoxy-Δ⁴,⁹-pregnadiene-3-one in 180 ml of glycol and 180 ml of ethyl orthoformate and the mixture was stirred at room temperature for 45 minutes under nitrogen. 10 ml of triethylamine were added thereto and the mixture was evaporated to dryness under reduced pressure. The residue was added over one hour to 500 ml of iced water and the mixture was poured with stirring into 2 liters of iced water containing pyridine. The mixture was stirred at 0° C. and was then vacuum filtered. The product was washed and dried to obtain 50.5 g of product. The latter was dissolved in 10 ml of refluxing isopropyl ether containing 0.1% of triethylamine and the mixture was cooled and filtered to obtain 450 mg of 3,3-ethylenedioxy-17α-methyl-20R-acetoxy-19-nor-Δ⁵,⁹-pregnadiene melting at 148° C. and having a specific rotation of $[\alpha]_D^{20} = +121° \pm 3.5°$ (c=0.5% in chloroform).

STEP B:
3,3-ethylenedioxy-5α,10α-epoxy-17α-methyl-20R-acetoxy-19-nor-Δ⁹⁽¹¹⁾-pregnene 2.5 ml of hexafluoroacetone sesquihydrate and 1 ml of 85% oxygenated water and then 0.1 ml of pyridine were added at 0° C. to a mixture of 40 g of the product of Step A in 200 ml of methylene chloride containing 0.1 ml of pyridine and the mixture was stirred at 0° C. for 6 to 7 hours and was then poured into a mixture of 1.5 liters of 0.2M sodium thiosulfate solution, 500 g of ice and 1 ml of pyridine. The mixture was stirred at room temperature for 10 minutes and the decanted aqueous phase was extracted with methylene chloride. The extract was washed with aqueous 0.2M sodium thiosulfate solution, dried and evaporated to dryness under reduced pressure. The 44 g of residue were taken up in 40 ml of isopropyl ether containing 0.1% of pyridine at 60° C. The mixture was cooled to room temperature and was filtered to obtain 27.6 g of 3,3-ethylenedioxy-5α,10α-epoxy-17α-methyl-20R-acetoxy-19-nor-Δ⁹⁽¹¹⁾-pregnene melting at 166° C. and having a specific rotation of $[\alpha]_D^{20} = -4.5° \pm 1°$ (c=1% in chloroform).

STEP C:
3,3-ethylenedioxy-11β-(3-methoxyphenyl)-17α-methyl-20R-acetoxy-19-nor-Δ⁹-pregnene-5α-ol Using the process of preparation 1, 7.5 g of the product of Step B and 80 ml of a solution of 0.9M of 3-methoxyphenyl magnesium bromide per liter of tetrahydrofuran were reacted with stirring at −20° C. for 18 hours to obtain after pressure chromatography 5.4 g of 3,3-ethylenedioxy-11β-(2-methoxyphenyl)-17α-methyl-20R-acetoxy-19-norΔ⁹-pregnene-5α-ol which after crystallization from ether melted at 160° C. and had a specific rotation of $[\alpha]_D^{20} = +19.5° \pm 1°$ (c=1% in chloroform).

PREPARATION 55

Cyclic 1,2-ethanediylacetal of 3-(dimethylamino-prop-1-ynyl)-11β-(3-methoxyphenyl)-17α-Δ⁹-estrene-5α,17-diol-3-one

STEP A:
3,3-ethylenedioxy-11β-(3-methoxyphenyl)-Δ⁹-estrene-5α-ol-17-one

A mixture of 5 g of 3,3-ethylenedioxy-5α,10α-epoxy-Δ⁹⁽¹¹⁾-estrene-17-one, 50 ml of tetrahydrofuran, 310 mg of cupric chloride and 159 mg of lithium chloride was stirred at room temperature until dissolution occured and after cooling the mixture to −20° C., 31 ml of a solution of 0.75M of 3-methoxyphenyl magnesium bromide per liter of tetrahydrofuran was added thereto dropwise. The mixture stood at −20° C. for one hour and after raising the temperature to −15° C., the same quantity of the magnesium solution was added to the mixture. The mixture was poured into a stirred iced aqueous ammonium chloride solution and the mixture was extracted with ether and then with methylene chloride. The organic phase was washed with aqueous saturated sodium chloride solution, dried and evaporated to dryness to obtain 3,3-ethylenedioxy-11β-(3-methoxyphenyl)-Δ⁹-estrene-5α-ol-17-one after chromatography.

STEP B: Cyclic 1,2-ethanediylacetal of 3-(dimethylamino-prop-1-ynyl)-11β-(3-methoxyphenyl)-Δ⁹-estrene-5α,17β-diol-3-one 3.9 ml of N,N-dimethylamino-propyne were slowly added at −50° C. to 30 ml of a solution of 0.67M of diisopropylamide lithium [J. Org. Chem., Vol. 43 (1978), p. 704] per liter of ether and the temperature was allowed to rise to 0° C. The mixture was then cooled to −40° C. and a solution of 4 g of the product of Step A in 11 ml of tetrahydrofuran was added thereto dropwise. The temperature rose over one hour to 0° C. and the mixture was poured into 500 ml of aqueous saturated ammonium chloride solution. The mixture was extracted with ethyl acetate and the organic phase was washed with aqueous saturated sodium chloride solution, dried and evaporated to dryness under reduced pressure to obtain 4.9 g of residue. 600 mg of the residue were chromatographed over silica gel and eluted with a 92-8 methylene chloride-methanol mixture to obtain 200 mg of cyclic 1,2-ethanediylacetal of 3-(dimethylamino-prop-1-ynyl)-11β-(3-methoxyphenyl)-Δ⁹-estrene-5α,17β-diol-3-one with a specific rotation of $[\alpha]_D^{20} = -62° \pm 2.5°$ (c=0.5% in chloroform).

Analysis: Calculated: %C 73.6; %H 8.3, Found: % 73.3; %H 8.3.

PREPARATION 57

3,3-ethylenedioxy-11β-(4-hydroxyphenyl)-17α-(prop-1-ynyl)-Δ⁹-estrene-5α,17β-diol A solution of 7.8 g of p-bromophenol in 15 ml of tetrahydrofuran and then 5.75 ml of trimethylsilyl chloride were added to 50 ml of a solution of 0.9M of isopropyl magnesium chloride per liter of tetrahydrofuran and the resulting solution was poured over 1.2 g of magnesium turnings. A little 1,2-dibromoethane and then 2 ml of hexamethylphosphortriamide were added to the mixture which was refluxed for 2½ hours to obtain a solution of 4-trimethylsilyloxy-phenyl magnesium bromide.

350 mg of cupric chloride and then a solution of 1.45 g of 3,3-ethylenedioxy-5α,10α-epoxy-17α-(prop-1-ynyl)-Δ$^{9(11)}$-estrene-17β-ol in 15 ml of tetrahydrofuran were added to 75 ml of the above solution and the mixture was poured into aqueous ammonium chloride solution. The mixture was extracted with ether and the organic phase was washed with aqueous N sodium hydroxide solution, dried and evaporated to dryness under reduced pressure. The residue was chromatographed over silica gel and eluted with a 7-3 benzene-ethyl acetate mixture to obtain 207 mg of 3,3-ethylenedioxy-11β-(4-hydroxyphenyl)-17α-(prop-1-ynyl)-Δ$^9$-estrene-5α,17β-diol having a specific rotation of $[\alpha]_D^{20} = -58.5° \pm 2.5°$ (c=0.5% in chloroform).

Analysis: $C_{29}H_{36}O_5$ Calculated: %C 74.97; %H 7.81; Found: %C 75.0; %H 7.9.

EXAMPLE 1

11β-(2-thienyl)-17α-(prop-1-ynyl)-Δ$^{4,9}$-estradiene-17β-ol-3-one

A mixture of 9.85 g of the product of Preparation 1 and 330 ml of 95% ethanol was heated to reflux and 9.85 g of Redex CF resin were added thereto all at once. The mixture was refluxed under nitrogen with stirring for 4 hours and was filtered. The filter was rinsed with ethanol and the filtrate was evaporated to dryness under reduced pressure to obtain 9 g of residue. The latter was chromatographed over silica gel and eluted with a 9-1 chloroform-ethyl acetate mixture to obtain 6.5 g of product which was crystallized from isopropyl ether. The mixture was vacuum filtered and the product was rinsed with isopropyl ether and dried to obtain 5.315 g of 11β-(2-thienyl)-17α-(prop-1-ynyl)-Δ$^{4,9}$-estradiene-17β-ol-3-one melting at 192° C. and having a specific rotation of $[\alpha]_D^{20} = +83° \pm 2°$ (c=1% in chloroform).

Analysis: $C_{25}H_{28}O_2S$ Calculated: %C 76.5; %H 7.18; %S 8.16; Found: %C 76.4; %H 7.5; %S 8.0.

EXAMPLES 2 TO 35

Using the procedure of Example 1, the starting materials of the following Table were reacted to obtain the indicated products.

| Example | Starting Material of Preparation No. | Time of Reflux | Final Product | Melting point °C. | Specific Rotation $[\alpha]_D^{20}$ |
|---|---|---|---|---|---|
| 2 | 2 | 2 hours | 11β-(4-fluorophenyl)-17α-(prop-1-ynyl)-Δ$^{4,9}$-estradiene-17β-ol-3-one | 135-140° C. then 162 to 164° C. | + 19° ± 1.5° (c = 0.8% in CHCl$_3$) |
| 3 | 3 | 2 hours | 11β-(4-trifluoromethylphenyl)-17α-(prop-1-ynyl)-Δ$^{4,9}$-estradiene-17β-ol-3-one | 180° C. then 218° C. | +29° ± 1° (c = 1% in CHCl$_3$) |
| 4 | 4 | 90 minutes | 11β-methyl-17α-(prop-1-ynyl)-Δ$^{4,9}$-estradiene-17β-ol-3-one | 213° | −153° ± 2.5° (c = 1.5% in CHCl$_3$) |
| 5 | 5 | one hour | 11β-(propa-1,2-dienyl)-17α-(prop-1-ynyl)-Δ$^{4,9}$-estradiene-17β-ol-3-one | 133° | +122° ± 2° (c = 0.9% in CHCl$_3$) |
| 6 | 6 | one hour | 11β-tert.-butyl-17α-(prop-1-ynyl-)Δ$^{4,9}$-estradiene-17β-ol-3-one | 168° | −152° ± 2.5° (c = 1% in CHCl$_3$) |
| 7 | 7 | one hour | 11β-(2-furyl)-17α-(prop-1-ynyl)-Δ$^{4,9}$-estradiene-17β-ol-3-one | 208° | +2.5° ± 1° (c = 1% in CHCl$_3$) |
| 8 | 8 | 90 minutes | 11β-(4-methylphenyl)-17α-(prop-1-ynyl)-Δ$^{4,9}$-estradiene-17β-ol-3-one | 232° | +70° C.± 1.5° (c = 1% in CHCl$_3$) |
| 9 | 9 | 2 hours | 11β-(3-methylphenyl)-17α-(prop-1-ynyl)-Δ$^{4,9}$-estradiene-17β-ol-3-one | 182° | +35° ± 1° (c = 1% in CHCl$_3$) |
| 10 | 10 | 45 minutes | 11β-(4-chlorophenyl)-17α-(prop-1-ynyl)-Δ$^{4,9}$-estradiene-17β-ol-3-one | 214° | +87° ± 2.5° (c = 0.5% in CHCl$_3$) |
| 11 | 11 | 2 hours | 11β-(5-chlorothienyl)-17α-(prop-1-ynyl)-Δ$^{4,9}$-estradiene-17β-ol-3-one | — | +115.5° ± 2° (c = 1% in CHCl$_3$) |
| 12 | 12 | 45 minutes | 11β-(3-chlorophenyl)-17α-(prop-1-ynyl)-Δ$^{4,9}$-estradiene-17β-ol-3-one | Calculated: % C 77.03 % H 6.94 % Cl 8.42 Found: % C 76.8 % H 7.0 % Cl 8.4 | +44° ± 2.5° (c = 0.5% in CHCl$_3$) |
| 13 | 13 | 90 minutes | 11β-(3-methoxy-phenyl-17α-(prop-1-ynyl-Δ$^{4,9}$-estradiene-17β-ol-3-one | 120° | +45° ± 1° (c = 1% in CHCl$_3$) |
| 14 | 14 | 90 minutes | 11β-(4-methoxyphenyl)-17α-(prop-1-ynyl)-Δ$^{4,9}$-estradiene-17β-ol-3-one | ≈120° | +73° ± 2° (c = 1% in CHCl$_3$) |
| 15 | 15 | 75 minutes | 11β-(3,4-dimethoxyphenyl)-17α-(prop-1-ynyl)-Δ$^{4,9}$-estradiene-17β-ol-3-one | 209° | +53.5° ± 1.5° (c = 1.2% in CHCl$_3$) |
| 16 | 16 | 45 minutes | 11β-(3-trifluoromethylphenyl)-17α-(prop-1-ynyl)-Δ$^{4,9}$-estradiene-17β-ol-3-one | 202° | +21.5° ± 1° (c = 0.9% in CHCl$_3$) |
| 17 | 17 | one hour | 11β-(3-trifluoromethyl-4-chloro- | 188° | +69° ± 2.5° (c = |

-continued

| Example | Starting Material of Preparation No. | Time of Reflux | Final Product | Melting point °C. | Specific Rotation $[\alpha]_D^{20}$ |
|---|---|---|---|---|---|
| | | | phenyl)-17α-(prop-1-ynyl)-$\Delta^{4,9}$-estradiene-17β-ol-3-one | | 0.7% in CHCl$_3$) |
| 18 | 18 | 30 minutes | 11β-(2-naphthyl)-17α-(prop-1-ynyl)-$\Delta^{4,9}$-estradiene-17β-ol-3-one | 170° | +252° ± 4° (c = 1% in CHCl$_3$) |
| 19 | 19 | one hour | 11β-(4-phenoxyphenyl)-17α-(prop-1-ynyl)-$\Delta^{4,9}$-estradiene-17β-ol-3-one | — | +73.5° ± 1.5° (c = 0.8% in CHCl$_3$) |
| 20 | 20 | 1 hour | 11β-phenyl-17α-(prop-1-ynyl)-$\Delta^{4,9}$-estradiene-17β-ol-3-one | 190° | +35.5° ± 2° (c = 0.5% in CHCl$_3$) |
| 21 | 21 | 1 hour | 11β-(3-bromophenyl)-17α-(prop-1-ynyl)-$\Delta^{4,9}$-estradiene-17β-ol-3-one | Calculated: % C 69.67 % H 6.28 % Br 17.17 Found: % C 69.7 % H 6.3 % Br 17.2 | +45.5° ± 1.5° (c = 1% in CHCl$_3$) |
| 22 | 22 | 75 minutes | 11β-(4-bromophenyl)-17α-(prop-1-ynyl)-$\Delta^{4,9}$-estradiene-17β-ol-3-one | 214° | +88.5° ± 2° (c = 1% in CHCl$_3$) |
| 23 | 23 | 1 Hour | 11β-(4-methylthiophenyl)-17α-(prop-1-ynyl)-$\Delta^{4,9}$-estradiene-17β-ol-3-one | 148–150° | +135° ± 2.5° (c = 1% in CHCl$_3$) |
| 24 | 24 | 2 hours | 11β-(3-thienyl)-17α-(prop-1-ynyl)-$\Delta$4,9-estradiene-17β-ol-3-one | 202° | +91.5% ± 2° (c = 1% in CHCl$_3$) |
| 25 | 25 | 1 hour | 11β-propyl-17α-(prop-1-ynyl)-$\Delta^{4,9}$-estradiene-17α-ol-3-one | 141° | −146.5° ± 2.5° (c = 0.75% in CHCl$_3$) |
| 26 | 26 | 90 minutes | 11β-(3-fluorophenyl)-17α-(prop-1-ynyl)-$\Delta^{4,9}$-estradiene-17β-ol-3-one | 172° | +25° ± 2° (c = 0.5% in CHCl$_3$) |
| 27 | 27 | 90 minutes | 11β-(3-phenoxyphenyl)-17α-(prop-1-ynyl)-$\Delta^{4,9}$-estradiene-17β-ol-3-one | Calculated: % C 82.81 % H 7.16 Found: % C 82.6 % H 7.3 | +51° ± 1.5° (c = 0.95% in CHCl$_3$) |
| 28 | 28 | 1 hour | 11β-(4-phenylphenyl)-17α-(prop-1-ynyl)-$\Delta^{4,9}$-estradiene-17β-ol-3-one | 240° | +181.5° ± 3° (c = 1% in CHCl$_3$) |
| 29 | 29A | 35 minutes | 11β-(2-methyl-prop-1-enyl)-17β-(prop-1-ynyl)-$\Delta^{4,9}$-estradiene-17β-ol-3-one | Calculated: % C 82.24 % H 8.63 Found: % C 82.1 % H 8.5 | −212.5° ± 3° (c = 1% in CHCl$_3$) |
| 30 | 30A | 1 hour | 11β-(3-methoxyphenyl)-19-nor-$\Delta^{4,9}$-pregnadiene-17β-ol-3,20-dione | 173° | +108.5° ± 2.5° (c = 0.5% in CHCl$_3$) |
| 31 | 31 | 1 hour | 11β-propyl-17α-methyl-19-nor-$\Delta^{4,9}$-pregnadiene-3,20-dione | 122° Calculated: % C 81.31 % H 9.67 Found: % C 81.3 % H 9.7 | −105° ± 2° (c = 1% in CHCl$_3$) |
| 32 | 32 | 2½ hours | 11β-(4-methylthiophenyl)-17α-methyl-19-nor-$\Delta^{4,9}$-pregnadiene-3,20-dione | Calculated: % C 77.37 % H 7.88 % S 7.38 Found: % C 77.6 % H 8.0 % S 7.4 | +263° ± 4.5° (c = 0.6% in CHCl$_3$) |
| 33 | 33 | 1 hour | 11β,16α-dimethyl-19-nor-$\Delta^{4,9}$-pregnadiene-3,20-dione | 155° | Rf = 0.26 |
| 34 | 34 | 1 hour | 11β-(4-methylthiophenyl)-16α-methyl-19-nor-$\Delta^{4,9}$-pregnadiene-3,20-dione | Calculated: % C 77.37 % 7.88 % S 7.38 Found: % C 77.6 % H 8.0 % S 7.4 | +290° ± 5° (c = 0.6% in CHCl$_3$) |
| 35 | 35 | 1 hour | 11α-cyclopropyl-17α-(prop-1-ynyl)-$\Delta^{4,9}$-estradiene-17β-ol-3-one | Calculated: % C 82.24 % H 8.63 Found: % C 82.2 % 8.7 | Rf = 0.28 |

EXAMPLE 36

Tert.-butyl [11β-(3-methoxyphenyl-3-oxo-17α-(prop-1-ynyl)-17β-$\Delta^{4,9}$-estradiene-17-yl]-oxyacetate A mixture of the product of Preparation 36, 40 ml of methanol and 4 ml of 2N hydrochloric acid was stirred for one hour at room temperature and was then poured into aqueous 0.5N sodium bicarbonate solution. The mixture was stirred for 5 minutes and was extracted with ether. The organic phase was washed with aqueous saturated sodium chloride solution, dried and evaporated to dryness under reduced pressure. The residue was chromatographed over silica gel and eluted with 97-3 petroleum ether (b.p.=60°–80° C.)-ethyl acetate mixture to obtain 720 mg of tert.-butyl [11β-(3-methoxyphenyl)-3-oxo-17α-(prop-1-ynyl)-17β-$\Delta^{4,9}$-estradiene-17-yl]-oxyacetate which was used as is for Example 37.

EXAMPLE 37

[11β-(3-methoxyphenyl)-3-oxo-17α-(prop-1-ynyl)-17β-Δ$^{4,9}$-estradiene-17-yl]-oxyacetic acid A mixture of 5 g of the product of Example 36, 500 mg of p-toluenesulfonic acid and 100 ml of benzene was refluxed for 5 hours and was evaporated to dryness under reduced pressure. The resin residue was chromatographed over silica gel and eluted with a 92.5-7.5 methylene chloride-methanol mixture to obtain 886 mg of [11β-(3-methoxyphenyl)-3-oxo-17α-(prop-1-ynyl)-17β-Δ$^{4,9}$-estradiene-17-yl]-oxyacetic acid with a specific rotation of $[\alpha]_D^{20} = +50.5°$ (c=0.3% in chloroform).

EXAMPLE 38

Sodium [11β-(3-methoxyphenyl)-3-oxo-17α-(prop-1-ynyl)-17β-Δ$^{4,9}$-estradiene-17-yl]-oxyacetate A mixture of 305 mg of the product of Example 37 and 3 ml of 0.2 moles of sodium ethanolate was stirred until dissolution occured and the mixture was filtered. The filtrate was evaporated to dryness under reduced pressure and the residue was triturated with isopropyl ether until solidification occured. The mixture was stirred and vacuum filtered and the product was rinsed with isopropyl ether and dried to obtain 280 mg of sodium [11β-(3-methoxyphenyl)-3-oxo-17α-(prop-1-ynyl)-17β-Δ$^{4,9}$-estradiene-17-yl]-oxyacetate melting at >270° C.

Analysis: Calculated: %Na 4.63; Found: %Na 4.45.

EXAMPLES 39 TO 43

Using the procedure of Example 2, the compounds in the following Table were prepared.

mixture was washed with aqueous 0.5N sodium thiosulfate, with aqueous saturated sodium bicarbonate solution and was dried and evaporated to dryness under reduced pressure. The residue was chromatographed over silica gel and eluted with a 95-5 methylene chloride-acetone mixture to obtain 1.075 g of 9α,10α-epoxy-11β-(4-methoxyphenyl)-17α-(prop-1-ynyl)-Δ$^4$-estrene-17β-ol-3-one which after crystallization from a methanol-isopropyl ether mixture melted at 185°-189° C.

EXAMPLE 45

9α,10α-epoxy-11β-(4-methylsulfonylphenyl)-17α-(prop-1-ynyl)-Δ$^4$-estrene-17β-ol-3-one 960 mg of 85% m-chloro-perbenzoic acid were added in small fractions over 5 minutes at 0° C. to a solution of 570 mg of 11β-(4-methylthiophenyl)-17α-(prop-1-ynyl)-Δ$^{4,9}$-estradiene-17β-ol-3-one (Example 23) in 13 ml of methylene chloride and after stirring the mixture for 90 minutes under nitrogen at 0° C., it was poured with stirring into 100 ml of 0.5M sodium thiosulfate solution. The mixture was stirred a few minutes at room temperature and was extracted with methylene chloride. The organic phase was washed with aqueous sodium bicarbonate solution, dried and evaporated to dryness under reduced pressure. The residue was chromatographed over silica gel and eluted with a 1-1 benzene-ethyl acetate mixture to obtain 750 mg of 9α,10α-epoxy-11β-(4-methylsulfonylphenyl)-17α-(prop-1-ynyl)-Δ$^4$-estrene-17β-ol-3-one which after crystallization from an isopropyl ether-methylene chloride mixture melted at 205°-208° C. and had a specific rotation of $[\alpha]_D^{20} = +67.5° \pm 1.5°$ (c=1% in chloroform).

EXAMPLE 46

Syn (Z) and anti (E) isomers of

| Example | Starting Material of Preparation No. | Time of Reflux | Final Product | Melting point °C. | Specific Rotation $[\alpha]_D^{20}$ |
|---|---|---|---|---|---|
| 39 | 39 | 45 minutes | 11β-(4-isopropylphenyl)-17α-(prop-1-ynyl)-Δ$^{4,9}$-estradiene-17β-ol-3-one | 192° | +73.2° ± 2° (c = 0.7% in CHCl₃) |
| 40 | 40 | 1 hour | 11β-(3-methylthiophenyl)-17α-(prop-1-ynyl)-Δ$^{4,9}$-estradiene-17β-ol-3-one | Calculated: % C 77.73 % H 7.45 Found: % C 77.7 % H 7.6 | +52° ± 1.5° (c = 1% in CHCl₃) |
| 41 | 41 | 40 minutes | 11β-(3-2-propenyloxyphenyl)-17α-(prop-1-ynyl)-Δ$^{4,9}$-estradiene-17β-ol-3-one | Calculated: % C 81.41 % H 7.74 Found: % C 81.7 % H 7.9 | +52.5° ± 2.5° (c = 0.7% in CHCl₃) |
| 42 | 42 | 30 minutes at 60° C. | 11β-thienyl 17α-methyl-19-nor-Δ$^{4,9(10)}$-pregnadiene-21-ol-3,20-dione | Calculated: % C 73.3 % H 7.5 % S 7.6 Found: % C 73.13 % H 7.36 % S 7.81 | +138.5° ± 3.5° (c = 0.57% in ethanol) |
| 43 | 43 | 1 hour | 11β-cyclopentyl-17α-(prop-1-ynyl)-Δ$^{4,9}$-estradiene-17β-ol-3-one | Calculated: % C 82.49 % H 9.05 Found: % C 82.2 % H 9.3 | +122° ± 2.5° (c = 0.9% in CHCl₃) |

EXAMPLE 44

9α,10α-epoxy-11β-(4-methoxyphenyl)-17α-(prop-1-ynyl)-Δ$^4$-estrene-17β-ol-3-one 700 mg of 85% m-chloro-perbenzoic acid were added in small fractions with stirring at 0° C. to a solution of 1.3 g of 11β-(4-methoxyphenyl)-17α-(prop-1-ynyl)-Δ$^{4,9}$-estradiene-17β-ol-3-one (Example 14) in 25 ml of methylene chloride and after one hour at 0° C., the temperature was allowed to rise to room temperature. The 3-methoxyimino-11β-(4-bromophenyl)-17α-(prop-1-ynyl)-Δ$^{4,9}$-estradiene-17β-ol 170 mg of methylhydroxylamine hydrochloride were added to a solution of 700 mg of the product of Example 22 in 10 ml of ethanol and the mixture was stirred at room temperature for 2 hours and was then poured into water. The mixture was extracted with ether and then with methylene chloride and the combined organic phases were dried and evaporated to dryness. The residue was chromatographed over silica gel and eluted with a 9-1 benzene-ethyl acetate mixture to obtain 408 mg of the anti (E) isomer of 3-methoxyimino-11β-(4-bromophenyl)-17α-(prop-1-ynyl)-Δ$^{4,9}$-estradiene-17β-ol melting at 185° C. and 200 mg of the corresponding syn (Z) isomer melting at 217° C.

Analysis: Anti product Calculated: %C 68.01; %H 6.52; %N 2.83; %Br 16.16; Found: %C 68.3; %H 6.6; %N 2.9; %Br 16.0.

EXAMPLE 47

Syn (Z) and anti (E) isomers of 3-hydroxyimino-11β-(3-fluorophenyl)-17α-(prop-1-ynyl)-Δ$^{4,9}$-estradiene-17β-ol 1.27 g of hydroxylamine hydrochloride were added all at once to a solution of 3.7 g of the product of Example 26 in 44.4 ml of absolute ethanol and 7.6 ml of pyridine and the mixture was refluxed for one hour, cooled to 0° C. and poured with stirring into 450 ml of an ice-water mixture. The mixture was extracted with methylene chloride and the organic phase was washed with water, dried and evaporated to dryness under reduced pressure. The residue was chromatographed over silica gel and eluted with a 7-3 cyclohexane-ethyl acetate mixture to obtain 2.7 g of the anti (E) isomer of 3-hydroxyimino-11β-(3-fluorophenyl)-17α-(prop-1-ynyl)-Δ$^{4,9}$-estradiene-17β-ol and 857 mg of syn (Z) isomer. The anti isomer was crystallized from a mixture of 20 ml of isopropyl ether and 10 ml of methylene chloride to obtain 2.145 g of the product melting at 210° C. and having a specific rotation of $[\alpha]_D^{20} = +35°\pm2.5°$ (c=0.5% in chloroform).

Analysis: Anti isomer Calculated: %C 77.3; %H 7.21; %N 3.34; Found: %C 77.3; %H 7.5; %N 3.3.

EXAMPLE 48

11β-(3-methoxyphenyl)-17α-methyl-20R-acetoxy-19-nor-Δ$^{4,9}$-pregnadiene-3-one

Using the procedure of Example 1, the compound of Preparation 48 was refluxed for 2 hours to obtain 11β-(3-methoxyphenyl)-17α-methyl-20R-acetoxy-19-nor-Δ$^{4,9}$-pregnadiene-3-one melting at 145° C. and having a specific rotation of $[\alpha]_D^{20} = +168°\pm2.5°$ (c=1% in chloroform).

Analysis: Calculated: %C 77.88; %H 8.28; Found: %C 77.6; %H 8.2.

EXAMPLE 49

11β-[4-(3-methylbutylthio)-phenyl]-17α-(prop-1-ynyl)-Δ$^{4,9}$-estradiene-17β-ol-3-one Using the procedure of Example 1, the product of Preparation 49 was refluxed for 45 minutes to obtain 11β-[4-(3-methylbutylthio)-phenyl]-17α-(prop-1-ynyl)-Δ$^{4,9}$-estradiene-17β-ol-3-one with a specific rotation of $[\alpha]_D^{20} = +133.5°\pm2.5°$ (c=1% in CHCl$_3$).

Analysis: Calculated: %C 78.62; %H 8.25; %S 6.56; Found: %C 78.4; %H 8.3; %S 6.4.

EXAMPLE 50

9α,10α-epoxy-11β-tert.-butyl-17α-(prop-1-ynyl)-Δ$^4$-estrene-17β-ol-3-one

Using the procedure of Example 44, 2.11 g of the product of Example 6 and 2.92 g of m-chloro-perbenzoic acid were reacted to obtain after chromatography 0.55 g of 9α,10α-epoxy-11β-tert.-butyl-17α-(prop-1-ynyl)-Δ$^4$-estrene-17β-ol-3-one melting at 186°–187° C. and having a specific rotation of $[\alpha]_d^{20} = +38°\pm1°$ (c=1% in chloroform).

Analysis: Calculated: %C 78.49; %H 8.96; Found: %C 78.4; %H 9.0.

EXAMPLE 51

9α,10α-epoxy-11β-cyclopentyl-17α-(prop-1-ynyl)-Δ$^4$-estrene-17β-ol-3-one

Using the procedure of Example 44, 1.5 g of the product of Example 43 and 0.8 g of m-chloro-perbenzoic acid were reacted to obtain after chromatography 0.7 g of 9α,10α-epoxy-11β-cyclopentyl-17α-(prop-1-ynyl)-Δ$^4$-estrene-17β-ol-3-one melting at 170° C. and having a specific rotation of $[\alpha]_D^{20} = +6.5°\pm1°$ (c=1% in chloroform).

Analysis: Calculated: %C 79.15; %H 8.68; Found: %C 79.6; %H 8.7.

EXAMPLE 52

9α,10α-epoxy-11β-(3-methoxyphenyl)-17α-(prop-1-ynyl)-Δ$^4$-estrene-17β-ol-3-one

Using the procedure of Example 44, 1.05 g of the product of Example 13 and 0.608 g of m-chloro-perbenzoic acid were reacted to obtain after chromatography 0.65 g of 9α,10α-epoxy-11β-(3-methoxyphenyl)-17α-(prop-1-ynyl)-Δ$^4$-estrene-17β-ol-3-one with a specific rotation of $[\alpha]_D^{20} = +43°\pm2.5°$ (c=0.6% in chloroform).

EXAMPLE 53

9α,10α-epoxy-11β-phenyl-17α-(prop-1-ynyl)-Δ$^4$-estrene-17β-ol-3-one

Using the procedure of Example 44, 1.15 g of the product of Example 20 and 0.608 g of m-chloro-perbenzoic acid were reacted to obtain after chromatography 0.85 g of 9α,10α-epoxy-11β-phenyl-17α-(prop-1-ynyl)-Δ$^4$-estrene-17β-ol-3-one in the form of crystals melting at 186°–187° C. and having a specific rotation of $[\alpha]_D^{20} = +47.5°\pm1.5°$ (c=1% in chloroform).

Analysis: Calculated: %C 80.56; %H 7.51; Found: %C 80.6; %H 7.3.

EXAMPLE 54

9α,10α-epoxy-11β-[4-(3-methyl-butylsulfonyl)-phenyl]-17α-(prop-1-ynyl)-Δ$^4$-estrene-17β-ol-3-one Using the procedure of Example 45, the product of Example 49 was reacted to obtain 9α,10α-epoxy-11β-[4-(3-methyl-butylsulfonyl)-phenyl]-17α-(prop-1-ynyl)-Δ$^4$-estrene-17β-ol-3-one melting at 174° C. and having a specific rotation of $[\alpha]_D^{20} = +62°\pm2.5°$ (c=0.6% in chloroform).

EXAMPLE 55

11β-(3-methoxyphenyl)-23-(N,N-dimethylamino)-19,21,24-trinor-17α-Δ$^{4,9}$-choladiene-20-yn-17β-ol-3-one A mixture of 4.3 g of the product of Preparation 55, 100 ml of methanol and 3 ml of 2N hydrochloric acid was stirred at room temperature for one hour and was then poured into a mixture of 300 ml of ethyl acetate and 200 ml of aqueous 0.25M sodium bicarbonate solution. The decanted aqueous phase was extracted with ethyl acetate and the combined organic phases were washed with aqueous saturated sodium chloride solution, dried and evaporated to dryness under reduced pressure. The residue was chromatographed over silica gel and eluted with a 95-5 acetone-ethyl acetate mixture to obtain 1.7 g of 11β-(3-methoxyphenyl)-23-(N,N-dimethylamino)-19,21,24-trinor-17α-Δ$^{4,9}$-choladiene-20-yn-17β-ol-3-one with a specific rotation of [α]$_D^{20}$=+40°±1° (c=1% in chloroform).

EXAMPLE 56

11β-(3-methoxyphenyl)-23-(N,N-dimethylamino)-19,21,24-trinor-17α-Δ$^{4,9}$-choladiene-20-yn-17β-ol-3-one hydrochloride A solution of 1.5 g of the product of Example 55 and 50 ml of ether was stirred at room temperature for 10 minutes and was filtered. 16.5 ml of gaseous hydrogen chloride in ether were added dropwise to the filtrate and the mixture was stirred for 10 minutes and was vacuum filtered. The product was rinsed with ether to obtain 1.4 g of the hydrochloride salt with a melting point of 190° C. and a specific rotation of [α]$_D^{20}$=+49°±2° (c=0.5% in water)

Analysis: Calculated: %C 72.63; %H 7.72; %N 2.82; Found: %C 72.5; %H 7.7; %N 2.7.

EXAMPLE 57

11β-(4-hydroxyphenyl)-17α-(prop-1-ynyl)-Δ$^{4,9}$-estradiene-17β-ol-3-one

A solution of 90 mg of the product of Preparation 57, 2 ml of methanol and 0.3 ml of 2N hydrochloric acid was stirred at room temperature for 2 hours and was then poured into an iced solution of 50% sodium bicarbonate solution. The mixture was extracted with ether and then with methylene chloride and the combined organic phases were washed with aqueous saturated sodium chloride solution, dried and evaporated to dryness under reduced pressure. The residue was chromatographed over silica gel and eluted witht a 92.5-7.5 methylene chloride-acetone mixture to obtain 71 mg of 11β-(4-hydroxyphenyl)-17α-(prop-1-ynyl)-Δ$^{4,9}$-estradiene-17β-ol-3-one with a specific rotation of [α]$_D^{20}$=+67° (c=0.25% in chloroform).

EXAMPLE 58

11β-(3-hydroxyphenyl)-17α-(prop-1-ynyl)-Δ$^{4,9}$-estradiene-17β-ol-3-one

STEP A:

3,3-ethylenedioxy-11β-[3-(2-tetrahydropyranyloxy)-phenyl]-17α-(prop-1-ynyl)-Δ$^9$-estrene-5α,17β-diol A mixture of 20.6 g of the tetrahydropyranyl ether of m-bromophenol and 160 ml of tetrahydrofuran was formed under nitrogen and 10 ml of the solution was poured over 2.2 g of magnesium turnings. After the reaction began, the rest of the solution was slowly added thereto while keeping the temperature at 52° C.±2° C. and the mixture was refluxed for 30 minutes and cooled to 20° C. to obtain a solution of the magnesium bromide.

36 g of anhydrous cupric chloride and 0.18 g of lithium chloride were added under an inert gas to a solution of 5.55 g of 3,3-ethylenedioxy-5α,10β-epoxy-17α-(prop-1-ynyl)-Δ$^{9(11)}$-estrene-17β-ol in 55 ml of tetrahydrofuran and 102 ml of the above magnesium bromide solution were added thereto at 0° to 3° C. over 30 minutes. The mixture was stirred at 0° C. for one hour and then 50 ml of aqueous ammonium chloride solution were added thereto. The decanted aqueous phase was extracted with ethyl acetate and the organic phase was washed with water, dried and evaporated to dryness. The residue was chromatographed over silica gel and eluted with a 95-5 methylene chloride-acetone mixture containing 1% of triethylamine to obtain 6.3 g of 3,3-ethylenedioxy-11β-[3-(2-tetrahydropyranyloxy)-phenyl]-17α-(prop-1-ynyl)-Δ$^9$-estrene-5α,17β-diol which after crystallization from ether melted at 216° C.

STEP B:

11β-(3-hydroxyphenyl)-17α-(prop-1-ynyl)-Δ$^{4,9}$-estradiene-17β-ol-3-one 5.5 g of Redex CF resin were added at 20° C. under an inert atmosphere to a suspension of 5.42 g of the product of Step A in 100 ml of 95% ethanol and the mixture was refluxed for 90 minutes and was filtered. The filtrate was evaporated to dryness and the residue was chromatographed over silica gel. Elution with a 1-1 cyclohexane-ethyl acetate mixture yielded 3.8 g of 11β-(3-hydroxyphenyl)-17α-(prop-1-ynyl)-Δ$^{4,9}$-estradiene-17β-ol-3-one which after crystallization from ethyl acetate and then acetone melted at 215° C. and had a specific rotation of [α]$_D^{20}$=+34.5°±1° (c=1% in chloroform).

Analysis: $C_{27}H_{30}O_3$; molecular weight=402.51 Calculated: %C 80.56; %H 7.51; Found: %C 80.5; %H 7.5.

EXAMPLE 59

Tablets were prepared containing 50 mg of the product of Example 23 and sufficient excipient of talc, starch and magnesium stearate for a final weight of 120 mg.

PHARMACOLOGICAL STUDY

I. Activity of products on hormonal receptors

A. Mineralcorticoidal receptor of kidneys of the rat

Male Sprague-Dawley EOPS rats weighing 140 to 160 g were surrenalectomized 4 to 8 days previously were killed and their kidneys were perfused in situ with 50 ml of a buffer (10 mM of Tris 0.25M of Saccharose and sufficient hydrochloric acid for a pH of 7.4). The kidneys were then removed, decapsulated and homogenized at 0° C. with a polytetrafluoroethylene-glass Potter (1 g of tissue per 3 ml of buffer). The homogenate was centrifuged for 10 minutes at 800 g at 0° C.

After elimination of the fixation of tritied aldosterone with glucocorticoid receptor, 21-methyl-Δ$^{1,4,6}$-pregnatrien-20-yne-11β,17β-diol-3-one fixed only with glucocorticoid receptor was added to the supernatant at a final concentration of 10$^{-6}$M. The supernatant was ultracentrifuged at 105,000 g for 60 minutes at 0° C. and aliquoits of the resulting surnatant were incubated at 0° C. with a constant concentration (T) of tritiated aldosterone in the presence of increasing concentrations (0-2500×10$^{-9}$M) of cold aldosterone or the cold test product. After a time (t) of incubation, the concentration of tied tritiated aldosterone (B) was measured by the technique of adsorption on carbon-dextran.

B. Androgen receptor of prostate of rats

Male Sprague-Dawley EPOS rats weighing 160 to 200 g were castrated and 24 hours later, the animals were killed. The prostates were removed, weighed and homogenized at 0° C. with a polytetrafluoroethylene-glass Potter with a buffered TS solution (Tris, 10 mM, 0.25M Saccharose, HCl-pH of 7.4) using 1 g of tissue per 5 ml of TS. The homogenate was then ultracentrifuged at 105,000 g after 60 minutes at 0° C. and aliquots of the resulting supernatant were incubated at 0° C. for an incubation time (E) with a constant concentration (T) of tritiated testosterone in the presence of increasing concentrations (0–1.000×10$^{-9}$M) of either cold testosterone or the test compound. The concentration of tied tritiated testosterone (B) was measured for each incubate by the technique of adsorption on carbon-dextran.

C. Progestogen receptor of the uterus of rabbits

Immature rabbits weighing about 1 kg received a cutaneous application of 25 μg of estradiol and the animals were killed 5 days later. The uterus were removed, weighed and homogenized at 0° C. with a polytetrafluoroethylene-glass Potter in a buffered TS solution [Tris 10 mM, 0.25M of saccharose, HCl-pH of 7.4] with 1 g of tissue per 50 ml of TS. The homogenate was ultracentrifuged at 105,000 g for 90 minutes at 0° C. and aliquoits of the resulting supernatant were incubated at 0° C. for a time (t) with a constant concentration (T) of tritiated product R or 17,21-dimethyl-19-nor-Δ$^{4,9}$-pregnadiene-3,20-dione in the presence of increasing concentrations (0 to 2500×10$^{-9}$M) of either cold R, cold progesterone or cold test compound. The concentration of tied tritiated R (B) was then measured for each incubate by the technique of adsorption on carbon-dextran.

D. Glucocorticoid receptor of thymus of rats

Male Sprague-Dawley EOPS rats weighing 160 to 200 g were surrenalectomized and the animals were killed 4 to 8 days later. The thymus were removed and homogenized at 0° C. in a buffered TS solution of 10 mM Tris, 0.25M of Saccharose, 2 mM of dithiothreitol, HCl for a pH of 7.4 using a polytetrafluoroethylene-glass Potter at a rate of 1 g of tissue per 10 ml of TS. The homogenate was ultracentrifuged at 105,000 g for 90 minutes at 0° C. and aliquoits of the resulting supernatant were incubated at 0° C. for a time (t) with a constant concentration (T) of tritiateddexamethasone in the presence of an increasing concentration (0 to 2500×10$^{-9}$M) of either cold dexamethasone or cold test product. The concentration of tied tritiated dexamethasone (B) was measured for each incubate by the adsorption on carbon-dextran technique.

E. Estrogen receptor of uterus of mice

Immature female mice 18 to 21 days old were killed and the uterus were removed and homogenized at 0° C. with a polytetrafluoroethylene-glass Potter in a buffered TS solution consisting of 10 mM Tris, 0.25M Saccharose, HCl for a pH of 7.4 at a rate of 1 g of tissue per 25 ml of TS. The homogenate was then ultracentrifuged at 105,000 g for 90 minutes at 0° C. and aliquots of the resulting tritiated were incubated at 0° C. for a time (t) with a constant concentration (T) of tritiated estradiol in the presence of increasing concentration (0 to 1000×10$^{-9}$M) of either cold estradiol or cold test compound. The concentration of tied tritiated estradiol (B) was measured for each incubate by the technique of adsoprtion on carbon-dextran.

The calculation of the relative affinity of concentration (ARL) was identical for all of the above receptor tests. One traced the following two curves: the percentage of tied tritiated hormone B/T as a function of the logarithm of the cold hormone concentration and B/T as a function of the logarithm of the concentration of the cold test product. One determined the line of the equation.

$$I_{50} = \frac{\frac{B}{T}\text{max.} + \frac{B}{T}\text{min.}}{2}$$

B/T max. is the percentage of tied tritiated hormone for an incubation of the hormone at concentration T B/T min. is the percentage of tied tritiated hormone for an incubation of the tritiated hormone at a concentration (T) in the presence of a large excess of cold hormone (2500×10$^{-9}$M).

The intersection of the $I_{50}$ line and the curves permits one to determine the concentrations of the cold hormone of the reference (CH) and the cold test compound (CX) which inhibit by 50% the tieing of tritiated hormone with the receptor. The relative affinity of tieing (ARL) of the test product was determined by the equation:

$$ARL = 100 \times \frac{CH}{CX}$$

The results are reported in the following Table.

| Products des example | Mineralo corticoid | | Androgen | | Pro- gestogen | | Gluco- corticoid | | Estrogen | |
|---|---|---|---|---|---|---|---|---|---|---|
| | 1 H | 24 H | ½ H | 24 H | 2 H | 24 H | 4 H | 24 H | 2 H | 5 H (25° C.) |
| 10 | 0,9 | 0,01 | 1,3 | 3 | 274 | 536 | 213 | 217 | ≦ | 0,01 |
| 11 | 1 | 0,1 | 11,5 | 1 | 160 | 80 | 274 | 249 | ≦ | 0,01 |
| 12 | 3,4 | 0,4 | 9,6 | 0,3 | 63 | 126 | 189 | 125 | ≦ | 0,01 |
| 23 | 0,4 | 0,04 | 6,3 | 12,4 | 236 | 910 | 210 | 227 | ≦ | 0,01 |
| 26 | 3,1 | 0,2 | 7,7 | 2,0 | 33 | 129 | 210 | 106 | ≦ | 0,01 |
| 28 | ≦0,01 | | ≦0,1 | 0,6 | 108 | 513 | 164 | 204 | ≦ | 0,01 |
| 32 | 1,9 | 0,7 | 1,1 | 3,0 | 66 | 230 | 42 | 27 | ≦ | 0,01 |
| 34 | 0,5 | 0,1 | 0,4 | 1,6 | 38 | 176 | 65 | 43 | ≦ | 0,01 |
| 35 | 0,02 | 0,02 | 0,6 | 0,4 | 11 | 9 | 186 | 128 | ≦ | 0,01 |
| 41 | 0,3 | 0,1 | 18 | 6,4 | 8,2 | 3,6 | 171 | 117 | ≦ | 0,01 |
| 44 | 1,4 | 0,1 | 13 | 5,6 | 41 | 67 | 136 | 140 | ≦ | 0,01 |
| 45 | 0,5 | 0,07 | 8,3 | 2,4 | 24 | 62 | 40 | 64 | ≦ | 0,01 |
| 47 | 0,35 | 0,04 | 0,13 | 0,05 | 19 | 16 | 160 | 100 | 3,5 | 0.80 |

The results of the above Table show that the tested compounds, especially the product of Example 23, present a very remarkable affinity for glucocorticoid and progestogen receptors as well as a moderate affinity for andogen receptors. The said results lead to the conclusion that the products present an agonist or antagonistic activity to glucocorticoids, progestogens and androgens.

III. Antiglucocorticoidal Activity

The test used was the test of Dauss et al [Molecular Pharmacology, Vol. 13 (1977), p. 948–955] entitled "The relationship between glucocorticoid structure and effects upon thymocytes" for mice thymocytes. The thymocytes of surrenalectomized rats were incubated at 37° C. for 3 hours in a nutritive medium containing $5 \times 10^{-8}$M of dexamethasone in the presence or absence of the test compound at different concentrations. Tritiated uridine was added and incubation was continued for one hour. The incubates were cooled and treated with a 5% trifluoroacetic acid solution and the mixture was filtered with Whatman GF/A paper. The filter was washed 3 times with a 5% trifluoroacetic acid solution and retained radioactivity on the filter was determined. Glucocorticoids and especially dexamethasone provoked a lessening of incorporation of tritiated uridine and the test compounds of Examples 10,11,12,23,26,32,34,35,41,44,45 and 47 opposed this effect as can be seen from the following Table.

| Product of Example | $5.10^{-8}$ Dexamethasone + concentration of test product | % of inhibition of the effect of Dexamethasone |
|---|---|---|
| 10 | $10^{-8}$ M | 9 |
|  | $10^{-7}$ M | 42 |
|  | $10^{-6}$ M | 89 |
| 11 | $10^{-8}$ M | 19 |
|  | $10^{-7}$ M | 61 |
|  | $10^{-6}$ M | 75 |
| 12 | $10^{-8}$ M | 11 |
|  | $10^{-7}$ M | 54 |
|  | $10^{-6}$ M | 85 |
| 23 | $10^{-8}$ M | 26 |
|  | $10^{-7}$ M | 64 |
|  | $10^{-6}$ M | 85 |
| 26 | $10^{-8}$ M | 11 |
|  | $10^{-7}$ M | 45 |
|  | $10^{-6}$ M | 93 |
| 32 | $10^{-8}$ M | 0 |
|  | $10^{-7}$ M | 4 |
|  | $10^{-6}$ M | 100 |
| 34 | $10^{-8}$ M | 0 |
|  | $10^{-7}$ M | 11 |
|  | $10^{-6}$ M | 68 |
| 35 | $10^{-8}$ M | 7 |
|  | $10^{-7}$ M | 22 |
|  | $10^{-6}$ M | 61 |
| 41 | $10^{-8}$ M | 15 |
|  | $10^{-7}$ M | 21 |
|  | $10^{-6}$ M | 100 |
| 44 | $10^{-8}$ M | 0 |
|  | $10^{-7}$ M | 23 |
|  | $10^{-6}$ M | 65,5 |
| 45 | $10^{-8}$ M | 13 |
|  | $10^{-7}$ M | 17 |
|  | $10^{-6}$ M | 49 |
| 47 | $10^{-8}$ M | 26 |
|  | $10^{-7}$ M | 76 |
|  | $10^{-6}$ M | 72 |

CONCLUSION

The products of the invention used alone do not provoke any effect of the glucocorticoid type and the tested products present a very remarkable antiglucocorticoid activity and are devoid of any glucocorticoid activity.

Various modifications of the products or methods of the invention may be made without departing from the spirit or scope thereof and it is to be understood that the invention is intended to be limited only as defined in the appended claims.

What we claim is:
1. A compound of the formula

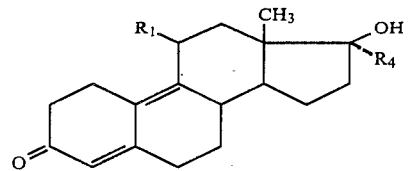

wherein $R_1$ is phenyl optionally substituted with at least one member of the group consisting of chlorine, fluorine, methylthio, methylsulfonyl, methoxy, hydroxy and allyloxy and $R_4$ is selected from the group consisting of ethynyl and propynyl with the proviso that when $R_4$ is ethynyl, $R_1$ is not phenyl or phenyl substituted with fluorine or methoxy.

2. A compound of claim 1 wherein $R_1$ is phenyl substituted with allyloxy.

3. A compound of claim 1 wherein $R_4$ is ethynyl.

4. A compound of claim 2 wherein $R_4$ is ethynyl.

5. A compound of claim 1 wherein $R_4$ is propynyl.

6. A compound of claim 2 wherein $R_4$ is propynyl.

7. A compound of claim 1 which is $11\beta$-[3-(2-propenyloxy)phenyl]-17$\alpha$-(prop-1-ynyl)-$\Delta^{4,9}$-estradiene-17$\beta$-ol-3-one.

8. A method of inducing antiprogestomimetic activity in warm-blooded animals comprising administering to warm-blooded animals an antiprogestiomimetically effective amount of at least one compound of claim 1.

9. The method of claim 8 wherein $R_1$ is phenyl substituted with allyloxy.

10. The method of claim 8 wherein $R_4$ is ethynyl.

11. The method of claim 8 wherein $R_4$ is propynyl.

12. The method of claim 9 wherein $R_4$ is ethynyl.

13. The method of claim 9 wherein $R_4$ is propynyl.

14. The method of claim 8 wherein the compound is $11\beta$-[3-(2-propenyloxy)phenyl]-17$\alpha$-(prop-1-ynyl)-$\Delta^{4,9}$-estradiene-17$\beta$-ol-3-one.

15. An antiprogestomimetic composition comprising an antiprogestiomimetically effective amount of at least one compound of claim 1.

16. A composition of claim 15 wherein $R_1$ is phenyl substituted with allyloxy.

17. A composition of claim 15 wherein $R_4$ is ethynyl.

18. A composition of claim 16 wherein $R_4$ is ethynyl.

19. A composition of claim 15 wherein $R_4$ is propynyl.

20. A composition of claim 16 wherein $R_4$ is propynyl.

* * * * *

UNITED STATES PATENT AND TRADEMARK OFFICE
CERTIFICATE OF CORRECTION

PATENT NO. : 4,540,686

DATED : Sept. 10, 1985

INVENTOR(S) : Daniel Philibert, Jean G. Teutsch, Germain Costerousse, and Roger Deraedt It is certified that error appears in the above-identified patent and that said Letters Patent is hereby corrected as shown below:

Col. Line

14
Preparation
15      Cols. 2, 3 & 4 should read as follows:

| Col. 2 | Col. 3 | Col. 4 |
|---|---|---|
| 3,3-ethylenebisoxy-5α,10α-epoxy-17α-(prop-1-ynyl)-$\Delta^{9(11)}$-estrene-17β-ol | 3,3-ethylenebisoxy-11β-(3,4-bismethoxyphenyl) 17α-(prop-1-ynyl)-$\Delta^9$-estrene 5α,17β-diol m.p. = 230°C $[\alpha]_D^{20}$ = -67° ±2° (c = 0.85% $CHCl_3$) | 2 hours at -15°C |

UNITED STATES PATENT AND TRADEMARK OFFICE
CERTIFICATE OF CORRECTION

PATENT NO. : 4,540,686

DATED : Sept. 10, 1985

Page 2 of 2

INVENTOR(S) : Daniel Philibert, Jean G. Teutsch, Germain Costerousse and Roger Deraedt It is certified that error appears in the above-identified patent and that said Letters Patent is hereby corrected as shown below:

| Col. | Line | | |
|---|---|---|---|
| 20 | 9 | "7.8 ml of a solution of one mole of hexa-" should start a new paragraph | |
| 25 | Example 29 | "17β" should be --17α-- | |
| | Example 30 | " " " " " " " " " " | |
| | Example 35 | "11α" should be --11β-- | |
| 34 | Col. 2 Col. 4 Col. 10 | should be | --Col. 2  Col.4  Col. 10 -- |

Signed and Sealed this

Eleventh Day of February 1986

[SEAL]

Attest:

DONALD J. QUIGG

Attesting Officer

Commissioner of Patents and Trademarks